(12) United States Patent
Hatala et al.

(10) Patent No.: US 8,207,298 B2
(45) Date of Patent: Jun. 26, 2012

(54) METHODS OF SEPARATING BIOPOLYMER CONJUGATED MOLECULES FROM UNCONJUGATED MOLECULES

(75) Inventors: Paul Hatala, Charlestown, MA (US); William J. Issa, Avon, MA (US)

(73) Assignee: Archemix Corp., Cambridge, MA (US)

( * ) Notice: Subject to any disclaimer, the term of this patent is extended or adjusted under 35 U.S.C. 154(b) by 383 days.

(21) Appl. No.: 12/434,170

(22) Filed: May 1, 2009

(65) Prior Publication Data

US 2009/0286955 A1 Nov. 19, 2009

Related U.S. Application Data

(60) Provisional application No. 61/126,227, filed on May 1, 2008.

(51) Int. Cl.
  *B01D 15/34* (2006.01)
  *C07H 1/06* (2006.01)
  *C07K 1/14* (2006.01)

(52) U.S. Cl. ....... 530/344; 210/690; 530/415; 536/25.4; 536/127

(58) Field of Classification Search .................. None
See application file for complete search history.

(56) References Cited

U.S. PATENT DOCUMENTS

| | | | |
|---|---|---|---|
| 5,668,264 A | 9/1997 | Janjic et al. | |
| 5,674,685 A | 10/1997 | Janjic et al. | |
| 5,948,231 A * | 9/1999 | Fuchs et al. | 204/601 |
| 6,207,816 B1 | 3/2001 | Gold et al. | |
| 6,229,002 B1 | 5/2001 | Janjic et al. | |
| 6,284,250 B1 * | 9/2001 | Lees et al. | 424/193.1 |

FOREIGN PATENT DOCUMENTS

| | | |
|---|---|---|
| WO | WO-9741102 A1 | 11/1997 |
| WO | WO 2005/090985 A1 * | 9/2005 |

OTHER PUBLICATIONS

Aslam et al., "The Functional Chemistry of Proteins and Protein Coupling/The Preparation of Protein-Small Molecule Conjugates", in *Bioconjugation Protein Coupling Techniques for the Biomedical Sciences*, Grove Dictionaries, Inc., New York, NY, Ch(s). 2 & 6 (1998).
Cotton et al., "2'-O-methyl, 2'-O-ethyl oligoribonucleotides and phosphorothiate oligodeoxyribonucleotides as inhibitors of the in vitro U7 snRNP-dependent mRNA processing event", *Nucl. Acids Res.*, 19:2629-2635 (1991).
Froehler et al., "Synthesis of DNA via deoxynucleoside H-phosphonate intermediates", *Nucl. Acids Res.*, 14(13):5399-5407 (1986).
Froehler, B.C., "Deoxynucleoside H-Phosphonate Diester Intermediates in the Synthesis of Internucleotide Phosphate Analogues", *Tet. Letters*, 27(46):5575-5578 (1986).

(Continued)

*Primary Examiner* — Jeffrey E Russel
(74) *Attorney, Agent, or Firm* — Mintz Levin Cohn Ferris Glovsky and Popeo, P.C.; Ivor R. Elrifi

(57) ABSTRACT

The invention relates to methods for separating or purifying biopolymer conjugated molecules from unconjugated molecules. In particular, methods are described for purifying a PEGylated protein or oligonucleotide from an unPEGylated protein or oligonucleotide, respectively. The methods are quick and efficient separation methods because they do not require gradient chromatography, fractionation of an eluent or analysis of the eluted fractions. Further, the methods increase yield and purity of the biopolymer conjugated molecule.

55 Claims, 11 Drawing Sheets standard PEGylation multiple PEGylation dimerization via PEGylation

OTHER PUBLICATIONS

Hirose et al., "Rapid Synthesis of Trideoxyribonucleotide Blocks", *Tet. Letters*, 28:2449-2452 (1978).

Hobbs et al., "Polynucleotides containing 2'-amino-2'-deoxyribose and 2'-azido-2'-deoxyribose", *Biochem.*, 12(25):5138-5145 (1973).

Hoekstra et al., "Potent, Orally Active GPIIb/IIIa Antagonists Containing a Nipecotic Acid Subunit. Structure-Activity Studies Leading to the Discovery of RWJ-53308", *J. Med. Chem.*, 42(25):5254-5265 (1999).

Roberts et al., "Chemistry for peptide and protein PEGylation", *Adv. Drug Del. Rev.*, 54:459-476 (2002).

Sood et al., "A rapid and convenient synthesis of poly-thymidylic acid by the modified triester approach", *Nucl. Acids Res.*, 4(8):2757-2765 (1977).

Sproat et al., "New synthetic routes to synthons suitable for 2'-O'allyloligoribonucleotide assembly", *Nucl. Acids Res.*, 19(4):733-738 (1990).

Zablocki et al., "Potent in vitro and in vivo Inhibitors of Platelet Aggregation Based Upon the ARG-GLY-ASP Sequence of Fibrinogen. (Aminobenzamidino)Succinyl (ABAS) Series of Orally Active Fibrinogen Receptor Antagonists", *J. Med. Chem.*, 38(13):2378-2394 (1995).

* cited by examiner

METHODS OF SEPARATING BIOPOLYMER CONJUGATED MOLECULES FROM UNCONJUGATED MOLECULES

CROSS-REFERENCE TO RELATED APPLICATIONS

This non-provisional patent application claims the benefit of and priority to U.S. Provisional Patent Application Ser. No. 61/126,227, filed May 1, 2008, which is incorporated herein by reference in its entirety.

FIELD OF THE INVENTION

The invention relates to methods for separating or purifying biopolymer conjugated molecules from unconjugated molecules. In particular, methods are described for purifying a PEGylated protein or oligonucleotide from an unPEGylated protein or oligonucleotide, respectively. The methods are quick and efficient separation methods because they do not require gradient chromatography, fractionation of an eluent or analysis of the eluted fractions. Further, the methods increase yield and purity of the biopolymer conjugated molecules.

BACKGROUND OF THE INVENTION

Current methods for separating biopolymer conjugated molecules (e.g., PEGylated molecules) from unconjugated molecules (e.g., unPEGylated molecules) require many steps. For example, such methods include the following steps: 1) preparative purification of the unconjugated molecule by ion-exchange high performance liquid chromatography (HPLC) under gradient conditions, with collection of fractions, 2) analysis of the fractions by analytical HPLC, 3) pooling of the fractions and analytical HPLC analysis of the appropriate fraction pools, 4) desalting of the appropriate fraction pool, 5) lyophilization of the unconjugated molecule, 6) conjugating a biopolymer to the molecule (e.g., PEGylating the molecule), 7) application of the crude biopolymer (e.g., PEG) reaction mixture to another ion-exchange HPLC under gradient conditions, with collection of the fractions, 8) analyzing the fractions by analytical HPLC, 9) pooling of the fractions and analysis by analytical HPLC, 10) performing ultrafiltration and desalting, and 11) lyophilizing the biopolymer conjugated molecule (e.g., PEGylated molecule). Every purification will decrease the total yield of the desired product because some fractions will inevitably contain a mixture of products. In addition, the analysis of the individual fractions and fraction pools increases time spent in a manufacturing plant, as well as the cost of the analysis itself.

For large scale (e.g., GMP (good manufacturing practices)) manufacturing of biopolymer conjugated molecules, streamlining the aforementioned protocol would result in a significant reduction in both production cost and time. Those skilled in the art of process chemistry and engineering will recognize the need to eliminate purifications and reduce the number of overall unit operations. Accordingly, there is a need for the development of quick and efficient processes for the purification in high yield and purity of biopolymer conjugated molecules, such as, for example, oligonucleotides, such as aptamers, and proteins that are conjugated to polyethylene glycol moieties.

BRIEF DESCRIPTION OF THE DRAWINGS

FIG. 30 (middle) shows the flowover containing ARC7299, which is approximately 91% pure. FIG. 30 (bottom) shows the material bound to the resin, which contains about 15% full length product.

FIG. 31 (middle) shows the flowover containing ARC5692, which is approximately 90% pure. FIG. 31 (bottom) shows the material bound to the resin, which contains trace amounts of full length product.

SUMMARY OF THE INVENTION

Figure 1:
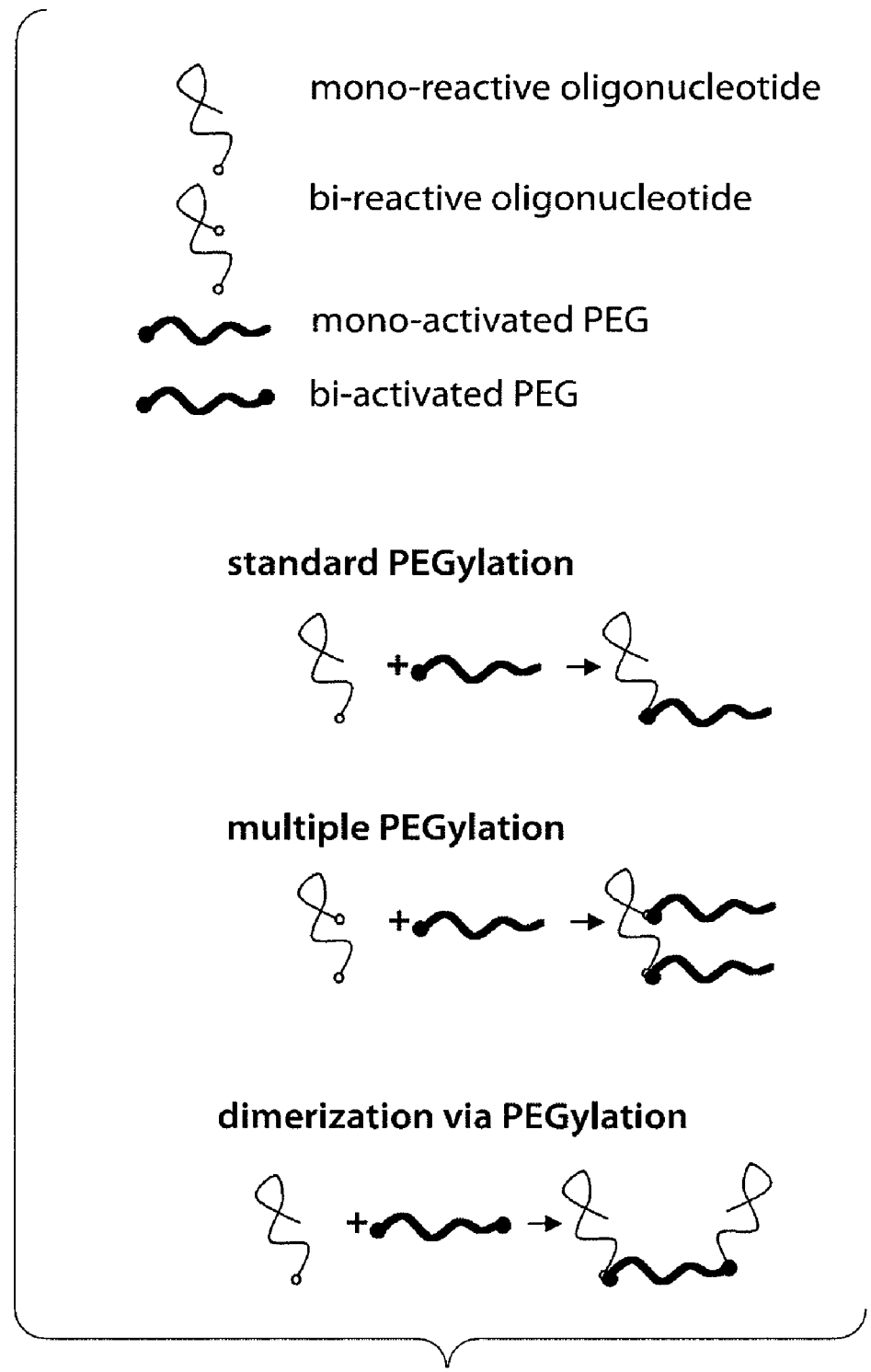
FIG. 1 illustrates some strategies for synthesizing PEGylated nucleic acid aptamers.

The invention relates to methods for separating or purifying biopolymer conjugated molecules from unconjugated molecules. The methods of the invention separate or purify biopolymer conjugated molecules from unconjugated molecules without the need to perform traditional gradient chromatography in order to elute the biopolymer conjugated molecules. Therefore, there is no need to collect, analyze and pool eluted fractions, while increasing yield and purity of the biopolymer conjugated molecules. These methods comprise applying a mixture containing a biopolymer conjugated molecule and an unconjugated molecule to a resin, wherein the biopolymer conjugated molecule is substantially excluded from the resin and the unconjugated molecule is substantially captured by the resin. The methods of the invention are also referred to herein as "Load and Flow".

Specifically, the methods of the invention comprise the steps of applying a mixture containing a biopolymer conjugated molecule and an unconjugated molecule to a resin having a pore size and a charge that substantially captures the unconjugated molecule with such pore size that also substantially excludes the biopolymer conjugated molecule from the resin, wherein the unconjugated molecule is substantially captured by the resin and the biopolymer conjugated molecule is substantially excluded from the resin; and collecting the entire filtrate as a single fraction, thereby separating a biopolymer conjugated molecule from an unconjugated molecule in the absence of gradient chromatography, and recovering the biopolymer conjugated molecule. Therefore, the filtrate includes the portion of the mixture that remains after the mixture has been applied to the resin and the unconjugated molecule has been substantially captured by the resin. The resin is designed or selected so as to (i) bind or otherwise interact with the unconjugated molecule and retain the unconjugated molecule, such that the unconjugated molecule is not displaced by washing or other techniques and (ii) not substantially bind or otherwise interact with the biopolymer conjugated molecule, such that the biopolymer conjugated molecule remains in the filtrate.

The unconjugated molecule may be any type or size of molecule. Preferably, the molecule is a peptide, polypeptide or protein. Alternatively, the molecule is an oligonucleotide. Most preferably, the molecule is an aptamer. Preferably, the unconjugated molecule ranges in size from 1-100 kDa. For example, the unconjugated molecule has a size in a range selected from 1-50 kDa, 50-100 kDa, 1-25 kDa, 25-50 kDa, 50-75 kDa, 75-100 kDa, 1-10 kDa, 1-20 kDa, 1-30 kDa, 1-40 kDa, 1-60 kDa, 1-70 kDa, 1-80 kDa, 1-90 kDa, 5-15 kDa, 5-25 kDa, 5-35 kDa, 5-45 kDa, 5-55 kDa, 10-20 kDa, 20-30 kDa, 30-40 kDa, 40-50 kDa, 50-60 kDa, 60-70 kDa, 70-80 kDa, 80-90 kDa and 90-100 kDa. However, the size of an aptamer is unlikely to be over 25 kDa while the size of a protein is unlikely to be over 100 kDa.

The biopolymer may be any type, size or configuration of biopolymer. Preferably, the biopolymer is a polyalkylene glycol biopolymer. Most preferably, the biopolymer is a polyethylene glycol biopolymer. Preferably, the biopolymer ranges in size from 1-100 kDa. For example, the biopolymer has a size in a range selected from 1-50 kDa, 50-100 kDa, 1-25 kDa, 25-50 kDa, 50-75 kDa, 75-100 kDa, 1-10 kDa, 1-20 kDa, 1-30 kDa, 1-40 kDa, 1-60 kDa, 1-70 kDa, 1-80 kDa, 1-90 kDa, 5-15 kDa, 5-25 kDa, 5-35 kDa, 5-45 kDa, 5-55 kDa, 10-20 kDa, 20-30 kDa, 30-40 kDa, 40-50 kDa, 50-60 kDa, 60-70 kDa, 70-80 kDa, 80-90 kDa and 90-100 kDa. Most preferably, the biopolymer is 20 kDa in size or greater. For example, the biopolymer has a size selected from 20 kDa, 25 kDa, 30 kDa, 35 kDa, 40 kDa, 45 kDa, 50 kDa, 55 kDa, 60 kDa, 70 kDa and 80 kDa. Preferably, the biopolymer is linear or branched.

In some embodiments, the conjugated and unconjugated molecules are conjugated and unconjugated oligonucleotides, respectively. In other embodiments, the conjugated and unconjugated molecules are conjugated and unconjugated proteins or polypeptides, respectively. In further embodiments, the conjugated and unconjugated molecules are PEGylated and unPEGylated molecules, respectively.

The mixture can be any reaction mixture that contains both conjugated and unconjugated molecules. Usually, the mixture is a crude reaction mixture that contains unconjugated molecules, biopolymer conjugated molecules and unreacted biopolymers. Preferably, the crude reaction mixture contains unPEGylated molecules, PEGylated molecules and unreacted PEGs.

The mixture can contain any concentration of biopolymer conjugated molecule. Preferably, the concentration of biopolymer conjugated molecule in the mixture is at least 30%. For example, the concentration of biopolymer conjugated molecule in the mixture is less than 75%, 70%, 65%, 60%, 55%, 50%, 45%, 40%, 35% or 30%.

The resin can be any type of resin that is used for separating or purifying molecules provided that the resin has a pore size and a charge that substantially captures the unconjugated molecule with such pore size that also substantially excludes the biopolymer conjugated molecule from the resin, such that the unconjugated molecule is substantially captured by the resin and the biopolymer conjugated molecule is substantially excluded from the resin. The resin may comprise a column (as in solid phase extraction methods), but need not be contained in a column (as in batch mode methods). Preferably, the resin comprises a column. More preferably, the column is a liquid chromatography column. Most preferably, the column is a high performance liquid chromatography column.

Further, the resin can be either an anion exchange resin or a cation exchange resin. In embodiments wherein the biopolymer is conjugated to an oligonucleotide, the resin is preferably an anion exchange resin. In some embodiments, the anion exchange resin is a strong anion exchange resin. In other embodiments, the anion exchange resin is a weak anion exchange resin. In embodiments wherein the biopolymer is conjugated to a peptide, polypeptide or protein, the resin is preferably a cation exchange resin. In some embodiments, the cation exchange resin is a strong cation exchange resin. In other embodiments, the cation exchange resin is a weak cation exchange resin.

The methods of the invention comprise the step of applying a mixture to a resin. The resin may comprise a column, as in solid phase extraction (SPE) embodiments. However, the resin need not be contained in a column, as in batch mode embodiments. Preferably, the applying step comprises flowing the mixture over the resin. Alternatively, the mixture and resin may be stirred or agitated to create a slurry.

The mixture may, optionally, be diluted before being applied to the resin. Preferably, the diluent is water, sodium hydroxide, solvent or buffer.

The buffer is preferably selected from the group consisting of phosphate buffer, citrate, formate, acetate, MES (2-[N-morpholino]ethanesulfonic acid), Bis-Tris (bis(2-hydroxyethyl)iminotris-(hydroxymethyl)methane), PIPES (piperazine-N,N'-bis(2-ethanesulfonic acid), BES (N,N'-bis(2-hydroxyethyl)-2 aminoethanesulfonic acid), MOPS (3-(N-morpholino)propanesulfonic acid), HEPES (N-(2-hydroxyethyl)piperazine-N'-ethanesulfonic acid), Tris, ammonia, borate, diethylamine, Ada (N-(2-acetaamido)iminodiacetic acid), Aces (N-(2-acetamido)-2-aminoethanesulfonic acid), Ches (2-(cycleohexylamine) ethansulfonic acid) and Caps (3-(cyclohexylamino)-1-propanesulfonic acid). Most preferably, the buffer is selected from the group consisting of citrate, formate, acetate, Tris, ammonia, borate and diethylamine.

The solvent is preferably selected from the group consisting of ethanol, acetonitrile, DMF, DMSO and methanol.

The methods of the invention may, optionally, further comprise the step of adding a denaturant to the mixture prior to applying the mixture to the resin. The denaturing step is preferred when the molecule conjugated to the biopolymer is an oligonucleotide. Preferably, the denaturant is either heat or a base. Suitable bases for use in the methods include, but are not limited to, sodium hydroxide, potassium hydroxide, lithium hydroxide, magnesium hydroxide and calcium hydroxide.

The methods of the invention achieve high yield and high purity. It is not uncommon to recover at least 75%, 80%, 85%, 90% or 95% of the biopolymer conjugated molecules from the mixture. Also, it is not uncommon that the recovered biopolymer conjugated molecule is at least 75%, 80%, 85%, 90% or 95% pure.

The method may, optionally, further comprise the step of separating the biopolymer conjugated molecule from the unreacted biopolymer. Preferably, the biopolymer conjugated molecule is separated from the unreacted biopolymer by HPLC, precipitation or liquid-liquid extraction.

The methods may, optionally, further comprise the step of analytical analysis of the final product, such as in release testing.

The methods may, optionally, also further comprise the step of removing the biopolymer from the biopolymer conjugated molecule.

The methods may, optionally, further comprise performing an ultrafiltration step and/or a desalting step.

The methods may, optionally, further comprise the step of lyophilizing the biopolymer conjugated molecule.

DETAILED DESCRIPTION OF THE INVENTION

The details of one or more embodiments of the invention are set forth in the accompanying description below. Although any methods and materials similar or equivalent to those described herein can be used in the practice or testing of the invention, the methods and materials are now described further. Other features, objects and advantages of the invention will be apparent from the description. In the description, the singular form also includes the plural, unless the context clearly dictates otherwise. Unless defined otherwise, all technical and scientific terms used herein have the same meaning as commonly understood by one of ordinary skill in the art to which this invention belongs. In the case of conflict, the present description will control.

DEFINITIONS

The terms below have the following meanings unless indicated otherwise.

The terms "oligonucleotide" and "polynucleotide" refer to oligomers of natural or modified nucleotides or of non-nucleotide analogs that are linked by phosphodiester bonds or analogs thereof that range in size from a few monomeric units to several hundred monomeric units. Typically, oligonucleotides will be 1-500 nucleotides in length. The oligonucleotide can be an aptamer.

An "aptamer" is a nucleic acid that has specific binding affinity to a target through interactions other than classic Watson-Crick base pairing. Aptamers are typically created by an in vitro selection process from pools of random sequence oligonucleotides. Aptamers have been generated for hundreds of targets, including growth factors, transcription factors, enzymes, immunoglobulins and receptors. A typical aptamer is 5-15 kDa in size (15-45 nucleotides), binds its target with sub-nanomolar affinity and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antigen-antibody complexes.

The terms "PEGylation" and "PEGylated" refer to the attachment of one or more polyethylene glycol (PEG) substituents, or derivatives thereof, to another molecule (e.g., an aptamer, protein or polypeptide). The terms "PAGylation" and "PAGylated" refer to the attachment of one or more polyalkylene glycol (PAG) substituents, or derivatives thereof, to another molecule (e.g., an aptamer, protein or polypeptide). Typical PAG polymers used in the invention include polyethylene glycol (PEG), also known as polyethylene oxide (PEO) and polypropylene glycol (including polyisopropylene glycol), and methoxypolyethylene glycol (mPEG). Additionally, random or block copolymers of different alkylene oxides (e.g., ethylene oxide and propylene oxide) can be used in many applications. In a common form, a polyalkylene glycol, such as PEG, is a linear polymer terminated at each end with hydroxyl groups: $HO-CH_2CH_2O-(CH_2CH_2O)_n-CH_2CH_2-OH$, wherein n ranges from 4 to 10,000. This polymer, alpha-, omega-dihydroxylpolyethylene glycol, can also be represented as HO-PEG-OH, where it is understood that the -PEG- symbol represents the following structural unit: $-CH_2CH_2O-(CH_2CH_2O)_n-CH_2CH_2-$, wherein n typically ranges from 4 to 10,000.

As shown above, the PAG molecule is di-functional and is sometimes referred to as "PAG diol". The terminal portions of the PAG molecule are relatively non-reactive hydroxyl moieties that can be activated, or converted to functional moieties, for attachment of the PAG to other compounds at reactive sites on the compounds. Such activated PAG diols are referred to herein as "bi-activated PAGs". For example, the terminal moieties of PAG diol have been functionalized as active carbonate esters for selective reaction with amino moieties by substitution of the relatively nonreactive hydroxyl moieties with succinimidyl active ester moieties from N-hydroxy succinimide. Alternatively, the PAG diols can be activated with a variety of groups, including without limitation α-halo acetic acids, epihalohydrines, maleates, tartrates and carbohydrates, which after appropriate manipulation would yield an activated carbonyl or equivalent for conjugation. Other methods of activating PAG are described in Roberts et al., (2002) Advanced Drug Deliver Reviews 54:549-476, which is incorporated herein by reference in its entirety. In addition to activating PAG using one of the previously described methods, one or both of the terminal alcohol functionalities of the PAG molecule can be modified to allow for different types of conjugation to a nucleic acid. For example, converting one of the terminal alcohol functionalities to an amine or a thiol allows access to urea and thiourethane conjugates.

In many applications, it is desirable to cap the PAG molecule on one end with an essentially non-reactive moiety so that the PAG molecule is mono-functional (or mono-activated). In the case of protein therapeutics, which generally display multiple reaction sites for activated PAGs, bi-functional activated PAGs lead to extensive cross-linking, yielding poorly functional aggregates. To generate mono-activated PAGs, one hydroxyl moiety on the terminus of the PAG diol molecule is typically substituted with a non-reactive methoxy end moiety, —$OCH_3$. The other, un-capped terminus of the PAG molecule is typically converted to a reactive end moiety that can be activated for attachment at a reactive site on a surface or a molecule, such as a protein. For example, mPEG: methoxy polyethylene glycol or $CH_3$—O—$(CH_2CH_2O)_n$ OH, wherein n ranges from 4 to 10,000.

The linear PEG molecule is di-functional and sometimes referred to as "PEG diol". The terminal portions of the PEG molecule are relatively non-reactive hydroxyl moieties that can be activated, or converted to functional moieties, for attachment of the PEG to other compounds at reactive sites on the compounds. Such activated PEG diols are referred to herein as "bi-activated PEGs". For example, the terminal moieties of PEG diol have been functionalized as active carbonate esters for selective reaction with amino moieties by substitution of the relatively non-reactive hydroxyl moieties with succinimidyl active ester moieties from N-hydroxy succinimide. Alternatively, the PEG diols can be activated with a variety of groups, including without limitation, α-halo acetic acids, epihalohydrines, maleates, tartrates and carbohydrates, which after appropriate manipulation would yield an activated carbonyl or equivalent for conjugation. Other methods of activating PEG are described in Roberts et al., (2002) Advanced Drug Deliver Reviews 54:549-476, which is incorporated herein by reference in its entirety. In addition to activating PEG using one of the previously described methods, one or both of the terminal alcohol functionalities of the PEG molecule can be modified to allow for different types of conjugation to a nucleic acid. For example, converting one of the terminal alcohol functionalities to an amine or a thiol allows access to urea and thiourethane conjugates.

In many applications, it is desirable to cap the PEG molecule on one end with an essentially non-reactive moiety so that the PEG molecule is mono-functional (or mono-activated). In the case of protein therapeutics, which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule is typically substituted with a non-reactive methoxy end moiety, —$OCH_3$. The other, un-capped terminus of the PEG molecule is typically converted to a reactive end moiety that can be activated for attachment at a reactive site on a surface or a molecule, such as a protein.

Most commonly, the synthesis of high molecular weight PEG-nucleic acid conjugates is accomplished by addition of a free primary amine at the 5'-terminus (incorporated using a modifier phosphoramidite in the last coupling step of solid phase synthesis). Using this approach, a reactive PEG (e.g., one that is activated so that it will react and form a bond with an amine) is combined with the purified oligonucleotide and the coupling reaction is carried out in solution. FIG. 1 illustrates strategies for synthesizing PEGylated nucleic acid aptamers. Other conjugation strategies include the coupling of: thiols to other thiols to form disulfides, thiols to malemides, thiols to vinyl sulfones, thiols to oxiranes or aziridines, amines to oxiranes, amines to aldehydes, and amines to isocyanates or isothiocyanates. See M Aslam, A Dent Bioconjugation, Grove Dictionaries, 1998. Preferably, the conjugation strategies include the coupling of: thiols to other thiols to form disulfides, and thiols to malemides.

In addition, high molecular weight PEG-nucleic acid-PEG conjugates can be prepared by reaction of a mono-functional activated PEG with a nucleic acid containing more than one reactive site. In one embodiment, the nucleic acid is bi-reactive and contains two reactive sites: a 5'-amino group and a 3'-amino group that are introduced into the oligonucleotide through conventional phosphoramidite synthesis, starting with a 3'-amine solid support, for example: 3'-5'-di-PEGylation. In alternative embodiments, reactive sites can be introduced at internal positions, using, for example, the 5-position of pyrimidines, the 8-position of purines or the 2'-position of ribose as sites for attachment of primary amines. In such embodiments, the nucleic acid can have several activated or reactive sites and is said to be multiply activated.

To produce a nucleic acid-PEG-nucleic acid conjugate, the nucleic acid is originally synthesized such that it bears a single reactive site (e.g., it is mono-activated). In one embodiment, this reactive site is an amino group that is introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In one embodiment, the concentration of oligonucleotide is 4 mM and the reconstituted solution contains 100 mM $NaHCO_3$ buffer, pH 8.5. Synthesis of the conjugate is initiated by slow, step-wise addition of highly purified bi-functional PEG. In another embodiment, the PEG diol is activated at both ends (bi-activated) by derivatization as p-nitrophenyl carbonate. Multiple PEG molecules concatenated, e.g., as random or block copolymers, can be linked to achieve various lengths (or molecular weights).

The terms "desalted" and "desalting" refer to the removal of salt or small molecules from a macromolecule. This is achieved, for example, by gel filtration, TFF (tangential flow filtration), UF/DF (ultrafiltration/diafiltration) or reverse phase HPLC.

As used herein, the term "pure" means an object species, such as the recovered biopolymer conjugated molecule, is the predominant species present (i.e., on a molar basis it is more abundant than any other individual species in the composition), and preferably a purified fraction is a composition wherein the object species comprises at least 50% (on a molar basis) of all macromolecular species present. Generally, a pure composition will comprise more than 75% of all macromolecular species present in the composition, and more preferably more than 80%, 85%, 90% and 95% of all macromolecular species present in the composition.

The terms "substantial" and "substantially" mean of ample or considerable amount, quantity, size, etc. For example, a substantial amount comprises at least 50%. Generally, a substantial amount comprises at least 75%. Preferably, a substantial amount comprises at least 80%, 85%, 90% or 95%.

Abbreviations

ACN: acetonitrile
DMF: N—N-dimethylformamide
DMSO: dimethylsulfoxide
FLP: full length product of an aptamer
HSA: human serum albumin
PEG: polyethylene glycol
mPEG: methoxy polyethylene glycol or $CH_3$—O$(CH_2CH_2O)_n$OH. mPEG attached to another atom is depicted as $CH_3$—O$(CH_2CH_2O)_n CH_2CH_2$—, wherein n is not 0 or 1.
HPLC: high performance liquid chromatography
SAX: Strong Anion eXchange HPLC
SPE: solid phase extraction

DESCRIPTION

The invention relates to methods for separating or purifying biopolymer conjugated molecules from unconjugated molecules. The methods of the invention separate or purify biopolymer conjugated molecules from unconjugated molecules without the need to perform traditional gradient chromatography in order to elute the biopolymer conjugated molecules. Therefore, there is no need to collect, analyze and pool eluted fractions, while increasing yield and purity of the biopolymer conjugated molecules. These methods comprise applying a mixture containing a biopolymer conjugated molecule and an unconjugated molecule to a resin, wherein the biopolymer conjugated molecule is substantially excluded from the resin and the unconjugated molecule is substantially captured by the resin. The methods of the invention are also referred to herein as "Load and Flow".

Specifically, the methods of the invention comprise the steps of applying a mixture containing a biopolymer conjugated molecule and an unconjugated molecule to a resin having a pore size and a charge that substantially captures the unconjugated molecule with such pore size that also substantially excludes the biopolymer conjugated molecule from the resin, wherein the unconjugated molecule is substantially captured by the resin and the biopolymer conjugated molecule is substantially excluded from the resin; and collecting the entire filtrate as a single fraction, thereby separating a biopolymer conjugated molecule from an unconjugated molecule in the absence of gradient chromatography, and recovering the biopolymer conjugated molecule. Therefore, the filtrate includes the portion of the mixture that remains after the mixture has been applied to the resin and the unconjugated molecule has been substantially captured by the resin. The resin is designed or selected so as to (i) bind or otherwise interact with the unconjugated molecule and retain the unconjugated molecule, such that the unconjugated molecule is not displaced by washing or other techniques and (ii) not substantially bind or otherwise interact with the biopolymer conjugated molecule, such that the biopolymer conjugated molecule remains in the filtrate.

The unconjugated molecule may be any type or size of molecule. For example, the types of molecules include, but are not limited to, peptides, polypeptides, proteins, oligonucleotides, aptamers, siRNA, antisense, small organic molecules, antibodies and lipids. Preferably, the molecule is a peptide, polypeptide or protein. Alternatively, the molecule is an oligonucleotide. Most preferably, the molecule is an aptamer. Preferably, the unconjugated molecule ranges in size from 1-100 kDa. For example, the unconjugated molecule has a size in a range selected from 1-50 kDa, 50-100 kDa, 1-25 kDa, 25-50 kDa, 50-75 kDa, 75-100 kDa, 1-10 kDa, 1-20 kDa, 1-30 kDa, 1-40 kDa, 1-60 kDa, 1-70 kDa, 1-80 kDa, 1-90 kDa, 5-15 kDa, 5-25 kDa, 5-35 kDa, 5-45 kDa, 5-55 kDa, 10-20 kDa, 20-30 kDa, 30-40 kDa, 40-50 kDa, 50-60 kDa, 60-70 kDa, 70-80 kDa, 80-90 kDa and 90-100 kDa. However, the size of an aptamer is unlikely to be over 25 kDa while the size of a protein is unlikely to be over 100 kDa.

The methods of the invention can be used with any type of peptide, polypeptide or protein, including modified peptides, polypeptides and proteins. Modifications include, but are not limited to, those that alter the size, charge and bonding capabilities of the amino acids that comprise the peptide, polypeptides or protein. In addition, modifications can include the use of non-standard amino acids, such as selenocysteine. Further modifications are well known to those of skill in the art.

Proteins, polypeptides and peptides used in the invention can be synthesized using any synthesis techniques known in the art, such as solid phase synthesis and liquid phase synthesis methods.

The methods of the invention can be used with any type of oligonucleotide or aptamer. For example, the oligonucleotides and aptamers may comprise standard, non-standard or modified nucleic acids. Preferably, the aptamer compositions are selected from the group consisting of: DNA, RNA, MNA, FNA, rRmY, dRmY, rGmH, fGmH, dGmH, dAmB, rRdY, dRdY, dCmD, rRfY and mRmY, where "MNA" refers to a nucleic acid molecule in which all nucleotides are 2'-O-methyl nucleotides (2'-OMe), "r" denotes a ribonucleotide (2'-OH), "d" denotes a deoxynucleotide, "f" denotes a 2'-fluoro nucleotide (2'-F), "m" denotes a 2'-OMe nucleotide, and "R," "Y," "H," "B," and "D" are as defined in Table 1 of the World Intellectual Property Organization Standard ST.25 ("Standard for the Presentation of Nucleotide and Amino Acid Sequence Listings in Patent Applications").

As stated previously, the methods of the invention can be used with modified oligonucleotides and modified aptamers. Modifications include, but are not limited to, those that provide other chemical groups that incorporate additional charge, polarizability, hydrophobicity, hydrogen bonding, electrostatic interaction and fluxionality to the nucleic acid ligand bases or to the nucleic acid ligand as a whole. Modifications to generate oligonucleotide populations that are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanosine. Modifications can also include 3' and 5' modifications, such as capping, e.g., addition of a 3'-dT cap to increase exonuclease resistance (see, e.g., U.S. Pat. Nos. 5,674,685; 5,668,264; 6,207,816 and 6,229,002; each of which is incorporated herein by reference in its entirety).

In some embodiments, oligonucleotides and aptamers are contemplated in which the P(O)O group is replaced by P(O)S ("thioate"), P(S)S ("dithioate"), P(O)NR$_2$ ("amidate"), P(O)R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotides through an —O—, —N— or —S-linkage. Not all linkages in the oligonucleotide are required to be identical.

In further embodiments, the oligonucleotides and aptamers comprise modified sugar groups, for example, one or more of the hydroxyl groups is replaced with a halogen, aliphatic group, or functionalized as an ether or an amine. In some embodiments, the 2'-position of the furanose residue is substituted with any of an O-methyl, O-alkyl, O-allyl, S-alkyl, S-allyl or halo group. Other 2'-modifications include 2'-fluoro and 2'-amino modifications. Methods for synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art.

The oligonucleotides and aptamers of the invention can be synthesized using any oligonucleotide synthesis techniques known in the art, including solid phase oligonucleotide synthesis techniques (see, e.g., Froehler et al., Nucl. Acid Res. 14:5399-5467 (1986) and Froehler et al., Tet. Lett. 27:5575-5578 (1986)) and solution phase methods, such as triester synthesis methods (see, e.g., Sood et al., Nucl. Acid Res. 4:2557 (1977) and Hirose et al., Tet. Lett., 28:2449 (1978)).

The biopolymer may be any type, size or configuration of biopolymer. For example, the types of biopolymers include, but are not limited to, polymers of: polyalkylene glycol, polyethylene glycol, polyoxazoline, hydroxyethyl starch and PolyPeg™. Preferably, the biopolymer is a polyalkylene glycol biopolymer. Most preferably, the biopolymer is a polyethylene glycol biopolymer. Preferably, the biopolymer ranges in size from 1-100 kDa. For example, the biopolymer has a size in a range selected from 1-50 kDa, 50-100 kDa, 1-25 kDa, 25-50 kDa, 50-75 kDa, 75-100 kDa, 1-10 kDa, 1-20 kDa, 1-30 kDa, 1-40 kDa, 1-60 kDa, 1-70 kDa, 1-80 kDa, 1-90 kDa, 5-15 kDa, 5-25 kDa, 5-35 kDa, 5-45 kDa, 5-55 kDa, 10-20 kDa, 20-30 kDa, 30-40 kDa, 40-50 kDa, 50-60 kDa, 60-70 kDa, 70-80 kDa, 80-90 kDa and 90-100 kDa. Most preferably, the biopolymer is 20 kDa in size or greater. For example, the biopolymer has a size selected from 20 kDa, 25 kDa, 30 kDa, 35 kDa, 40 kDa, 45 kDa, 50 kDa, 55 kDa, 60 kDa, 70 kDa and 80 kDa. Preferably, the biopolymer is linear or branched.

PEG derivatized compounds used in the invention are typically between 5 and 80 kDa in size, however any size can be used, the choice being dependent upon the molecule and application. Other PEG derivatized compounds used in the invention are between 10 and 80 kDa in size. Still other PEG derivatized compounds used in the invention are between 10 and 60 kDa in size. In some embodiments, PEG moieties derivatized to molecules of the invention are PEGs ranging in size from 10, 20, 30, 40, 50, 60, 70 or 80 kDa. In general, larger PEGs are preferred in the methods. For example, a 60 kDa PEG is better than a 40 kDa PEG, which is better than a 20 kDa PEG. In some embodiments, the PEG is linear, while in other embodiments, the PEG is branched.

Any type or number of molecules may be conjugated to any type or number of biopolymers. In some embodiments, the conjugated and unconjugated molecules are conjugated and unconjugated oligonucleotides, respectively. In other embodiments, the conjugated and unconjugated molecules are conjugated and unconjugated proteins or polypeptides, respectively. Preferably, the conjugated and unconjugated molecules are conjugated and unconjugated aptamers, respectively.

The biopolymer may be conjugated to any surface, area or position on the molecule. For example, the biopolymer may be conjugated to the amino terminus, the carboxy terminus, both the amino and carboxy termini, or at any internal amino acid on a peptide, polypeptide or protein. By way of further example, the biopolymer may be conjugated to the 5' end, 3' end, both the 5' and 3' ends, or at one or more internal sites of an oligonucleotide or aptamer.

In preferred embodiments, the conjugated and unconjugated molecules are PEGylated and unPEGylated molecules, respectively. In particularly preferred embodiments, the PEGylated and unPEGylated molecules are PEGylated and unPEGylated aptamers, respectively. In some embodiments, the PEG is attached to the 5' end of the aptamer, the 3' end of the aptamer, both the 5' and 3' ends of the aptamer, and/or one or more internal sites of the aptamer. Preferably, there is a single PEG attached to the 5' end of the aptamer, such as a 5'-amine PEGylated aptamer. More preferably, a single 40 kDa PEG is attached to the 5' end of an aptamer. Most preferably, a single 60 kDa PEG is attached to the 5' end of an aptamer. The PEG can be linear or branched. In yet further embodiments, more than one aptamer is conjugated to one PEG moiety, or more than one PEG moiety is conjugated to an aptamer.

The mixture can be any reaction mixture that contains both conjugated and unconjugated molecules. Usually, the mixture is a crude reaction mixture that contains unconjugated molecules, biopolymer conjugated molecules and unreacted biopolymers. Preferably, the crude reaction mixture contains unPEGylated molecules (which are just molecules), PEGylated molecules and unreacted PEGs.

The mixture can contain any concentration of biopolymer conjugated molecules. In certain embodiments, the mixture contains less than 75% biopolymer conjugated molecules. In some embodiments, the mixture contains less than 70% biopolymer conjugated molecules. In other embodiments, the mixture contains less than 65% biopolymer conjugated molecules. In further embodiments, the mixture contains less than 60% biopolymer conjugated molecules. In additional embodiments, the mixture contains less than 55% biopolymer conjugated molecules. In certain embodiments, the mixture contains less than 50% biopolymer conjugated molecules. In some embodiments, the mixture contains less than 45% biopolymer conjugated molecules. In other embodiments, the mixture contains less than 40% biopolymer conjugated molecules. In further embodiments, the mixture contains less than 35% biopolymer conjugated molecules. In additional embodiments, the mixture contains less than 30% biopolymer conjugated molecules.

The resin can be any type of resin that is used for separating or purifying molecules provided that the resin has a pore size and a charge that substantially captures the unconjugated molecule with such pore size that also substantially excludes the biopolymer conjugated molecule from the resin, such that the unconjugated molecule is substantially captured by the resin and the biopolymer conjugated molecule is substantially excluded from the resin. Numerous resins are known to those having skill in the art. The resin may comprise a column, as in solid phase extraction (SPE) embodiments, but need not be contained in a column, as in batch mode embodiments. Preferably, the resin comprises a column. More preferably, the column is a liquid chromatography column. Most preferably, the column is a high performance liquid chromatography column.

Further, the resin can be either an anion exchange resin or a cation exchange resin. In embodiments wherein the biopolymer is conjugated to an oligonucleotide, the resin is preferably an anion exchange resin. In some embodiments, the anion exchange resin is a strong anion exchange resin. In other embodiments, the anion exchange resin is a weak anion exchange resin. In embodiments wherein the biopolymer is conjugated to a peptide, polypeptide or protein, the resin is preferably a cation exchange resin. In some embodiments, the cation exchange resin is a strong cation exchange resin. In other embodiments, the cation exchange resin is a weak cation exchange resin.

According to preferred embodiments, the invention includes methods for separating a PEGylated protein from an unPEGylated protein, which comprise applying a mixture containing PEGylated and unPEGylated proteins to a cation exchange resin under conditions wherein the PEGylated protein is substantially excluded by the resin (because of its large size) and the unPEGylated protein is substantially captured by the resin (because of its smaller size and its electrostatic interactions with the resin). In one preferred embodiment, the cation exchange resin is a strong cation exchange resin. In another preferred embodiment, the cation exchange resin is a weak cation exchange resin.

According to other preferred embodiments, the invention includes methods for separating a PEGylated oligonucleotide from an unPEGylated oligonucleotide, which comprise applying a mixture containing PEGylated and unPEGylated oligonucleotides to an anion exchange resin under conditions wherein the PEGylated oligonucleotide is substantially excluded by the resin (because of its large size) and the unPEGylated oligonucleotide is substantially captured by the resin (because of its smaller size and its electrostatic interactions with the resin). In one preferred embodiment, the resin is a strong anion exchange resin. In another preferred embodiment, the resin is a weak anion exchange resin.

While it is not intended that the invention be limited by any specific mechanism, in embodiments wherein the biopolymer is conjugated to a protein, the cation exchange resin facilitates the separation of conjugated protein from unconjugated protein as a function of size and charge. The cation exchange resin has porous beads wherein the interior of the pores are rich with negative charges. When applied to this cation resin, substantially all of the conjugated proteins, by virtue of their size, cannot enter the negatively charged interior of the beads and, thereby, readily pass over the resin. However, the unconjugated proteins can pass through the pores, wherein the unconjugated proteins are electrostatically bound to the negative charges in the beads. In this respect, when the eluent is 100% $H_2O$, the unconjugated proteins will remain bound regardless of the volume of 100% $H_2O$ washes that may be passed through the cation resin. As a result, the material of interest, the biopolymer conjugated molecules, pass over the resin while the unwanted materials bind to the resin.

While it is not intended that the invention be limited by any specific mechanism, in embodiments wherein the biopolymer is conjugated to an oligonucleotide, the anion exchange resin facilitates the separation of conjugated oligonucleotide from unconjugated oligonucleotide as a function of size and charge. The anion exchange resin has porous beads wherein the interior of the beads are rich with positively charged groups. When applied to this anion exchange resin, substantially all of the conjugated oligonucleotides, by virtue of their size, cannot enter the positively charged interior of the beads and, thereby, readily pass over the resin. However, the unconjugated oligonucleotides do pass through the pores, wherein the unconjugated oligonucleotides are electrostatically bound to the positively charged groups. In this respect, when the eluent is 100% $H_2O$, the unconjugated oligonucleotides will remain bound regardless of the volume of 100% $H_2O$ washes that may be passed through the anion exchange resin. As a result, the material of interest, the biopolymer conjugated molecules, pass over the resin while the unwanted materials bind to the resin.

In embodiments wherein the biopolymer is conjugated to an oligonucleotide, the resin is an anion exchange resin. In some embodiments, the ion exchange group of the anion exchange resin is a strong anion exchanger. In a preferred embodiment, the ion exchange group comprises a quaternary amine group. For example, the quaternary amine group can be —$CH_2N^+(CH_3)_3$, as is in Q Sepharose® Fast Flow media (GE Healthcare), Q Sepharose® Big Beads media (GE Healthcare), Q Sepharose™ High Performance media (GE Healthcare) and Q Sepharose™ XL media (GE Healthcare). In another embodiment, the quaternary amine group may also contain other alkyl groups, such as, but not limited to, ethyl, propyl and butyl. In another embodiment, the quaternary amine group may also contain a combination of alkyl groups. In another embodiment, the resin is a polystyrene-divinylbenzene resin, such as Mono Q™ resin (GE Healthcare), or a methacrylate based resin. By way of illustration and without limitation, in certain embodiments for Q Sepharose™ resin, greater than 65 mg/mL of unPEGylated aptamer will bind to the resin, while about 1-5 mg/mL of PEGylated aptamer conjugated to, for example, 20 kDa or 40 kDa PEG moieties, respectively, will bind to the resin depending on the nature of the specific aptamer.

In other embodiments, the ion exchange group of the anion exchange resin is a weak anion exchanger. For example, the resin is DEAE Sepharose™ Fast Flow media (GE Healthcare) with the weak diethylaminoethyl anion exchanger, or ANX Sepharose™ Fast Flow media (GE Healthcare) with the weak diethylaminopropyl anion exchanger.

Preferably, Sepharose resins are used to separate unconjugated oligonucleotides from oligonucleotides that are conjugated to a 40K PEG.

In embodiments wherein the biopolymer is conjugated to a peptide, polypeptide or protein, the resin is a cation exchange resin. In some embodiments, the ion exchange group of the cation exchange resin is a strong cation exchanger. Examples of such resins include, but are not limited to, SP Sepharose® Fast Flow (GE Healthcare), SP Sepharose® High Performance (GE Healthcare), and SP Sepharose® XL (GE Healthcare) with a strong sulfopropyl —$(CH_2)_3SO_3^-$ strong cation exchanger or an exchanger comprised of another sulfate derivative.

In other embodiments, the ion exchange group of the cation exchange resin is a weak cation exchanger. Examples of such resins include, but are not limited to, CM Sepharose® Fast Flow (GE Healthcare) with a carboxymethyl —$CH_2COO^-$ weak anion exchanger or an exchanger comprised of carboxylate derived ions.

The methods of the invention comprise the step of applying a mixture to a resin. As stated previously, the resin may comprise a column, as in solid phase extraction (SPE) embodiments. However, the resin need not be contained in a column, as in batch mode embodiments. Preferably, the applying step comprises flowing the mixture over the resin.

In solid phase extraction embodiments, the mixture containing conjugated and unconjugated molecules is applied to the resin by flowing the mixture over the resin. In some embodiments, the resin is present in a column, such as an HPLC column. In some embodiments, the flow rate is between 50-500 cm/h. In preferred embodiments, the flow rate is between 150-250 cm/h. More preferably, the flow rate is between 150-400 cm/h. Most preferably, the flow rate is greater than 250 cm/h.

In particularly preferred SPE embodiments, a mixture containing PEGylated and un-PEGylated aptamers is applied to a resin by flowing the mixture over the resin. In some preferred embodiments, the resin is present in a column, such as an HPLC column. In a preferred embodiment, the flow rate is between 50-500 cm/h. In a more preferred embodiment, the flow rate is between 150-250 cm/h. In an even more preferred embodiment, the flow rate is between 150-400 cm/h. Most preferably, the flow rate is greater than 250 cm/h.

As stated previously, in some batch mode embodiments, the resin is not contained in a column. In these embodiments, the mixture containing conjugated and unconjugated molecules is added to a resin containing flask under conditions such that the mixture containing conjugated and unconjugated molecules and the resin are stirred or agitated so as to create a slurry. After a period of time, this stirring is discontinued and the resin is allowed to settle at the bottom of the flask. The supernatant is then transferred into another container and the purified biopolymer conjugated molecule is then recovered from the supernatant. In one embodiment, the supernatant is transferred by direct decanting. In another embodiment, the supernatant is transferred after the resin/conjugate mixture is centrifuged. In yet another embodiment, the supernatant is collected by filtration. In all cases, the resin can be washed with water or low concentration salt solutions.

In preferred batch mode embodiments (wherein the resin is not contained in a column), the conjugated and unconjugated molecules are PEGylated and unPEGylated aptamers or oligonucleotides. Alternatively, the conjugated and unconjugated molecules are PEGylated and unPEGylated proteins, polypeptides or peptides.

The mixture may, optionally, be diluted before being applied to the resin. It is not intended that the invention be limited to a specific diluent or combination of diluents. Examples of diluents are water, sodium hydroxide, solvent, buffer. Preferably, the diluent is water, sodium hydroxide, solvent or buffer.

The buffer may be any buffer known to those of skill in the art. However, the buffer is preferably selected from the group consisting of phosphate buffer, citrate, formate, acetate, MES (2-[N-morpholino]ethanesulfonic acid), Bis-Tris (bis(2-hydroxyethyl)iminotris-(hydroxymethyl)methane), PIPES (piperazine-N,N'-bis(2-ethanesulfonic acid), BES (N,N'-bis (2-hydroxyethyl)-2 aminoethanesulfonic acid), MOPS (3-(N-morpholino)propanesulfonic acid), HEPES (N-(2-hydroxyethyl)piperazine-N'-ethanesulfonic acid), Tris, ammonia, borate, diethylamine, Ada (N-(2-acetaamido)iminodiacetic acid), Aces (N-(2-acetamido)-2-aminoethanesulfonic acid), Ches (2-(cycleohexylamine)ethansulfonic acid) and Caps (3-(cyclohexylamino)-1-propanesulfonic acid). Most preferably, the buffer is selected from the group consisting of citrate, formate, acetate, Tris, ammonia, borate and diethylamine.

The solvent may be any solvent known to those of skill in the art. However, the solvent is preferably selected from the group consisting of ethanol, acetonitrile, DMF, DMSO and methanol.

It is not intended that the methods of the invention be limited to any specific factor of dilution for the mixture. In a preferred embodiment, the dilution of the mixture is between 0 and 10 fold. In a more preferred embodiment, the dilution of the mixture is 2-2.5 fold. In a most preferred embodiment, the dilution of the mixture is 3-4 fold.

In some specific embodiments, the diluent is both water and solvent. It is not intended that the diluent, comprising water and solvent, be limited to any specific solvent. In one embodiment, the solvent is a water soluble solvent. In a specific embodiment, the solvent component of the water and solvent mixture is less than or equal to 40% of the diluent by volume. In a specific embodiment, the solvent component of the water and solvent mixture is selected from the group consisting of: ethanol, acetonitrile, DMF, DMSO or methanol.

The methods of the invention may, optionally, further comprise the step of adding a denaturant to the mixture prior to applying the mixture to the resin. The denaturing step is preferred when the molecule conjugated to a biopolymer is an oligonucleotide. The purpose of the denaturing step is to facilitate binding of unconjugated molecules to the resin. The oligonucleotides may be denatured using any denaturant known in the art. Examples of denaturants include, but are not limited to, heat, base, urea. Preferably, the denaturant is either heat or a base. Examples of suitable bases for use in the methods include, but are not limited to, sodium hydroxide, potassium hydroxide, lithium hydroxide, magnesium hydroxide and calcium hydroxide.

Preferably, one of the following oligonucleotide denaturing conditions is used for the methods of the invention. If the denaturant is heat, the step preferably comprises equilibrating the column with water at 45-80° C. and loading the heated sample (45-80° C.) onto the column. If the denaturant is a base, the step preferably comprises equilibrating the column with 20-50 mM sodium hydroxide at ambient temperature and loading the sample onto the column (making sure to add sodium hydroxide to the mixture to make the concentration of sodium hydroxide in the mixture 20-50 mM prior to loading).

The methods of the invention achieve high yield and high purity. It is not uncommon to recover at least 75%, 80%, 85%, 90% or 95% of the biopolymer conjugated molecules from the mixture. Also, it is not uncommon that the recovered biopolymer conjugated molecule is at least 75%, 80%, 85%, 90% or 95% pure.

In specific embodiments of the invention, greater than 90% of the conjugated oligonucleotide in a mixture is recovered in a single sample volume from the total amount of conjugated oligonucleotide in a given volume of the mixture that is contacted with the resin. For example, greater than 91%, 92%, 93%, 94%, 95%, 96%, 97%, 98% or 99% of the conjugated oligonucleotide is recovered. In one embodiment, this single sample volume is the eluent from a chromatography column. In another embodiment, this single sample volume is the supernatant or filtrate of a batch process. In one embodiment, the single sample volume comprises: i) the eluted reaction mixture, ii) a single column volume wash of 100% $H_2O$ and iii) a single column volume wash with a buffer. In one embodiment, this buffer is: 60% of 100% $H_2O$ and 40% of a buffer containing 1.5 M NaCl and 20 mM sodium phosphate, pH 7.0.

In a preferred embodiment, a PEGylated aptamer is recovered in an aqueous solution or solvent mix between pH 6.0 and pH 12 For example, the pH is in a range of 6.0-7.0, 7.0-8.0, 8.0-9.0, 9.0-10.0, 10.0-11.0, or 11.0-12.0. In one embodiment, the buffer further contains 0% to 40% of 1.5 M NaCl or NaBr and 20 mM sodium phosphate, and/or 1.5 M NaCl or NaBr and sodium hydroxide. For example, the buffer contains between 0-10%, 10-20%, 20-30%, or 30-40% of 1.5 M NaCl or NaBr.

In particularly preferred embodiments, the oligonucleotides are aptamers. According to certain embodiments, the foregoing methods further comprise the step of recovering the polyalkylene conjugated molecule, such as the PEGylated aptamer. In one embodiment, the mixture applied to the resin is the crude product from a PEGylation reaction during which an aptamer is PEGylated. In one embodiment, about 97% of the PEGylated aptamer in the reaction mixture is recovered in a single sample volume from the total amount of PEGylated aptamer in a given volume of the reaction mixture that is contacted with the resin. In one embodiment, at least 95% of the PEGylated aptamer in the reaction mixture is recovered in a single sample volume from the total amount of PEGylated aptamer in a given volume of the reaction mixture that is contacted with the resin. In one embodiment, at least 90% of the PEGylated aptamer in the reaction mixture is recovered in a single sample volume from the total amount of PEGylated aptamer in a given volume of the reaction mixture that is contacted with the resin. In a preferred embodiment, the flow through, column wash, and 10% ion exchanger wash are collected in a single vessel containing only the desired PEGylated material.

In another preferred embodiment, the recovered PEGylated aptamer is at least 95% pure and more preferably at least 97% pure.

In preferred embodiments, the methods may be modified to maximize recovery of conjugated aptamers with different nucleotide compositions. While it is not intended that the invention be limited to aptamers of any specific composition, the methods of the invention may be adapted to optimize the recovery of PEGylated, DNA, RNA, MNA, FNA, rRmY, dRmY, rGmH, fGmH, dGmH, dAmB, rRdY, dRdY, dCmD, rRfY or mRmY containing aptamers. In one embodiment, the recovery of ribonucleotide containing aptamers is optimized by adjusting the pH of the reaction mixture to a range between 6.0 and 7.5 before contacting the reaction mixture with the resin. In a preferred embodiment, at least 5% of the nucleotides in the ribonucleotide containing aptamer are ribonucleotides. In a preferred embodiment, this ribonucleotide containing aptamer reaction mixture has a final buffer concentration between 5 and 250 mM. For example, the final buffer concentration is in a range of 5-50 mM, 50-100 mM, 100-150 mM, 150-200 mM, 200-250 mM, 5-25 mM, 25-45 mM, 45-65 mM, 65-85 mM, 85-105 mM, 105-125 mM, 125-145 mM, 145-165 mM, 165-185 mM, 185-205 mM, 205-225 mM or 225-250 mM. In one embodiment, the recovery of non-ribonucleotide containing aptamers is optimized by adjusting the pH of the reaction mixture to a range between 7.5 and 12.0 before contacting the reaction mixture with the resin. For example, the pH of the reaction mixture is in a range of 7.5-8.0, 8.0-8.5, 8.5-9.0, 9.0-9.5, 9.5-10.0, 10.0-10.5, 10.5-11.0, 11.0-11.5 or 11.5-12.0. In a preferred embodiment, this non-ribonucleotide containing aptamer reaction mixture has a final buffer concentration between 5 and 250 mM. For example, the final buffer concentration is in a range of 5-50 mM, 50-100 mM, 100-150 mM, 150-200 mM, 200-250 mM, 5-25 mM, 25-45 mM, 45-65 mM, 65-85 mM, 85-105 mM, 105-125 mM, 125-145 mM, 145-165 mM, 165-185 mM, 185-205 mM, 205-225 mM or 225-250 mM.

The method may, optionally, further comprise the step of separating the biopolymer conjugated molecule from the unreacted biopolymer. Any method known in the art for separating a biopolymer conjugated molecule from an unreacted biopolymer may be used. Preferably, the biopolymer conjugated molecule is separated from the unreacted biopolymer by HPLC, precipitation or liquid-liquid extraction.

The methods may, optionally, further comprise the step of analytical analysis of the final product, such as in release testing. For example, the filtrate may be analyzed by a variety of methods, including, but not limited to, analytical HPLC or LC methods, mass spec methods, LCMS methods, spectroscopic methods, UV/Vis, CD/ORD, atomic absorption, NMR, EPR, calorimetry and IR for characterization and release testing. For example, the filtrate may be analyzed for yield and purity of biopolymer conjugated molecule by analytical HPLC.

The methods may, optionally, also further comprise the step of removing the biopolymer from the biopolymer conjugated molecule. The purpose of this step is to isolate the unconjugated molecule from the biopolymer. This removal step can be accomplished by any method that is known to those of skill in the art.

The methods may, optionally, further comprise performing an ultrafiltration step and/or a desalting step. The purpose of the ultrafiltration step is to purify the biopolymer conjugated molecule biopolymer. The ultrafiltration step may be accomplished by any method that is known to those of skill in the art. The purpose of the desalting step is to remove salt from the biopolymer conjugated molecule. The desalting step may be accomplished by any method that is known to those having skill in the art.

The methods may, optionally, further comprise the step of lyophilizing the biopolymer conjugated molecule. The purpose of the lyophilization step is to preserve and store the biopolymer conjugated molecule. Lyophilization may be accomplished by any method that is known to those of skill in the art.

Particularly preferred embodiments of Load and Flow batch mode protocols are described below.

Using heat for oligonucleotide denaturation, a specific embodiment of the protocol is as follows:
1) Obtain a crude PEGylated reaction mixture at an oligonucleotide concentration of 2-10 mg/mL and between 40-70% abundance of PEGylated full length product (FLP);
2) Determine the abundance of reaction mixture consisting of unPEGylated material (1-0.01×% PEGylated FLP purity);
3) Calculate the appropriate Q Sepharose® Fast Flow resin volume to obtain 15-35 mg/mL loading of unPEGylated material (_ mg of unPEGylated material/_____ loading=_____ mL of resin);
4) To prepare the correct amount of resin for use:
   a) add slurried bulk resin (in 20% ethanol from manufacturer) to a conical vial and centrifuge for 30 minutes or let it gravity settle,
   b) pour off supernatant from settled resin and add or remove necessary amount of resin to achieve correct loading,
   c) reslurry in a volume of water equal to the volume of the resin, and centrifuge for 30 minutes or let gravity settle,
   d) pour off supernatant from settled resin and then add a volume of 1.5 M sodium chloride equal to the volume of the resin and reslurry,
   e) pour off supernatant from settled resin and then add a volume of water equal to the volume of the resin and reslurry,
   f) repeat step "e" twice to ensure all salt is removed from resin,
   g) to the settled resin, add a volume of water equivalent in volume to 20% of the resin volume and shake it to re-suspend the resin and achieve a slurry;
5) Add the crude PEGylated reaction mixture to the conical vial or transfer all contents to an appropriate Schott bottle;
6) Heat and vigorously shake at 45-80° C. for at least 20 minutes;
7) Re-slurry the mixture by shaking;
8) Filter the resin and wash the resin with 60-80° C. water;
9) Collect the filtrate; this is the desired PEGylated full length product;
10) To elute the unPEGylated impurities captured on the resin, sequentially wash the resin with 5× resin volume of each of the following eluents: 80° C. 500 mM sodium chloride, 80° C. 1 M sodium chloride, and 80° C. 1.5 M sodium chloride, collecting the filtrates of all of these elutions as one fraction; and 11) Confirm recovery and purity of desired product by UV spectroscopy and analytical SAX HPLC, respectively.

Using base for oligonucleotide denaturation, a specific embodiment of the protocol is as follows:

1) Obtain a crude PEGylated reaction mixture at an oligonucleotide concentration of 2-10 mg/mL and between 40-70% abundance of PEGylated full length product (FLP);
2) Determine the abundance of reaction mixture consisting of unPEGylated material (1-0.01×% PEGylated FLP purity);
3) Calculate the appropriate Q Sepharose® Fast Flow resin volume to obtain 15-35 mg/mL loading of unPEGylated material (_ mg of unPEGylated material/_____ loading=_____ mL of resin);
4) To prepare the correct amount of resin for use:
   a) add slurried bulk resin (in 20% ethanol from manufacturer) to a conical vial and centrifuge for 30 minutes or let it gravity settle,
   b) pour off supernatant from settled resin and add or remove necessary amount of resin to achieve correct loading,
   c) reslurry in a volume of water equal to the volume of the resin, and centrifuge for 30 minutes or let gravity settle,
   d) pour off supernatant from settled resin and then add a volume of 1.5 M sodium chloride 20 mM sodium hydroxide equal to the volume of the resin and re-slurry,
   e) pour off supernatant from settled resin and then add a volume of 20 mM sodium hydroxide equal to the volume of the resin and re-slurry,
   f) repeat step "e" twice to ensure all salt is removed from resin,
   g) to the settled resin, add a volume of 20 mM sodium hydroxide equivalent in volume to 20% of the resin volume and shake it to re-suspend the resin and achieve a slurry;
5) Spike the crude PEGylation reaction mixture with sodium hydroxide to make the final concentration of the loaded sample to be 20 mM sodium hydroxide;
6) Add the crude PEGylated reaction mixture to the conical vial or transfer all contents to an appropriate Schott bottle and vigorously shake for at least 20 minutes;
7) Re-slurry the mixture by shaking;
8) Filter the resin and wash the resin with 20 mM sodium hydroxide;
9) Collect the filtrate; this is the desired PEGylated full length product;
10) To elute the unPEGylated impurities captured on the resin, sequentially wash the resin with 5× resin volume of each of the following eluents: 500 mM sodium chloride, 20 mM sodium hydroxide, 1 M sodium chloride, 20 mM sodium hydroxide, 1.5 M sodium chloride, and 20 mM sodium hydroxide, collecting the filtrates of all of these elutions as one fraction; and
11) Confirm recovery and purity of desired product by UV spectroscopy and analytical SAX HPLC, respectively.

Particularly preferred embodiments of Load and Flow solid phase extraction protocols are described below.

Using heat for oligonucleotide denaturation, a specific embodiment of the protocol is as follows:

1) Obtain a crude PEGylated reaction mixture at an oligo concentration of 2-10 mg/mL and between 40-70% abundance of PEGylated full length product (FLP);
2) Determine the abundance of reaction mixture consisting of unPEGylated material (1-0.01×% PEGylated FLP purity);
3) Calculate the appropriate Q Sepharose® Fast Flow resin volume to obtain 15-35 mg/mL loading of unPEGylated material (_ mg of unPEGylated material/_____ loading=_____ mL of resin);
4) Pack empty Isolute SPE reservoirs (6, 15 or 25 mL) with a slurry containing the calculated volume of settled resin;
5) Turn on vacuum on solid phase extraction (SPE) kit;
6) To prep the resin for use:
   a) Run three column volumes of water over the column at ambient temperature,
   b) Run twenty column volumes of 80° C. water over the column,
   c) Run three column volumes of 80° C. 1.5 M sodium chloride over the column,
   d) Run ten column volumes of 80° C. water over the column to re-equilibrate the column;
7) Heat the PEGylation reaction mixture to 80° C. for 20 minutes prior to loading;
8) Load the crude PEGylation reaction mixture onto the column and collect the flowover in one fraction; this is the PEGylated full length product (FLP) of interest;
9) After loading, flow three column volumes of 80° C. water over the column to elute the rest of the desired PEGylated full length product (FLP) and continue collecting the flowover in the same fraction;
10) To elute the unPEGylated impurities captured on the resin, sequentially elute with three column volumes of each of the following eluents: 80° C. 500 mM sodium chloride, 80° C. 1 M sodium chloride, and 80° C. 1.5 M sodium chloride, collecting all of these elutions as one fraction;
11) Confirm recovery and purity of desired product by UV spectroscopy and analytical SAX HPLC, respectively.

Using aqueous base for oligonucleotide denaturation, a specific embodiment of the protocol is as follows:

1) Obtain a crude PEGylated reaction mixture at between 40-70% abundance of PEGylated full length product (FLP);
2) Determine the abundance of reaction mixture consisting of unPEGylated material (1-0.01×% PEGylated FLP purity);
3) Calculate the appropriate Q Sepharose® Fast Flow resin volume to obtain 15-35 mg/mL loading of unPEGylated material (_ mg of unPEGylated material/_____ loading=_____ mL of resin);
4) Pack empty Isolute SPE reservoirs (6, 15 or 25 mL) with a slurry containing the calculated volume of settled resin;
5) Turn on vacuum on solid phase extraction (SPE) kit;
6) To prep the resin for use:
   a) Run three column volumes of water over the column at ambient temperature,
   b) Run three column volumes of 20 mM sodium hydroxide over the column at ambient temperature,
   c) Run ten column volumes of 1.5 M sodium chloride, 20 mM sodium hydroxide over the column at ambient temperature,
   d) Run three column volumes of 20 mM sodium hydroxide over the column at ambient temperature to re-equilibrate the column;
7) Spike the crude PEGylation reaction mixture with sodium hydroxide to make the final concentration of the loaded sample to be 20 mM sodium hydroxide;
8) Load the crude PEGylation reaction mixture onto the column and collect the flowover in one fraction; this is the PEGylated full length product (FLP) of interest;
9) After loading, flow three column volumes of 20 mM sodium hydroxide over the column to elute the rest of the desired PEGylated full length product (FLP) and continue collecting the flowover in the same fraction;

10) To elute the unPEGylated impurities captured on the resin, sequentially elute with three column volumes of each of the following eluents: 500 mM sodium chloride, 20 mM sodium hydroxide, 1 M sodium chloride, 20 mM sodium hydroxide, 1.5 M sodium chloride, and 20 mM sodium hydroxide, collecting all of these elutions as one fraction;
11) Confirm recovery and purity of desired product by UV spectroscopy and analytical SAX HPLC, respectively.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. Those of skill in the art will recognize that the invention, having now been described by way of written description, can be practiced in a variety of embodiments and that the foregoing description and examples below are for purposes of illustration and not for limiting the scope of the claims.

EXAMPLES

Example 1

PEGylation of Oligonucleotides and Aptamers

The PEGylation of oligonucleotides, including aptamers, was accomplished with a para-nitrophenol activated PEG (PEG-PNP). This method is applicable to oligonucleotides containing a primary amine and is useful from small—(e.g., benchtop reactions) to large—(e.g., commercial) scale. At the 5' terminus of each synthesized oligonucleotide, a hexylamine linker that reacts with the activated PEG regent (PEG-PNP) was added, resulting in a carbamate linkage. The unPEGylated oligonucleotides were each dissolved to a concentration at or above 40 mg/ml in 100% water. Sodium bicarbonate buffer was added to a final concentration of 100 mM, pH 8.5. The reaction was performed under basic conditions in order to increase the nucleophilicity of the terminal amine present on the oligonucleotide. An equal volume of dimethylsulfoxide (DMSO) was added to each oligonucleotide containing solution. PEG-PNP was dissolved in acetonitrile, yielding an effective concentration of 200 mg/mL, which was then added to each oligonucleotide solution. Each reaction mixture was heated to 45° C. for 8-12 hours. PEG-PNP was added as needed to each reaction to drive the reaction to completion. The progress of each reaction was monitored using analytical Strong Anion eXchange (SAX) HPLC chromatography.

By way of example, aptamers were conjugated to 20 kDa linear and 40 kDa branched polyethylene glycol molecules (PEG) under very similar conditions.

Example 2

Purification of an Aptamer

Figure 2:
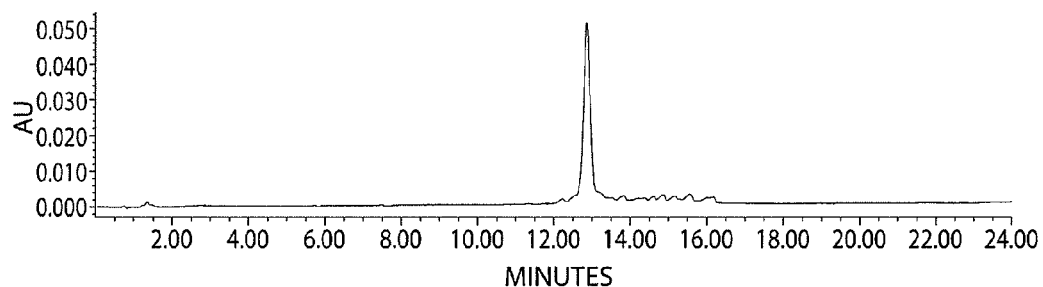
FIG. 2 is a SAX trace of the crude ARC5690 PEGylation reaction mixture prior to the purification described in Example 2.

The ARC5690 aptamer (a 33 mer) was synthesized and PEGylated as described in Example 1 with a 40 kDa PEG yielding 218.5 mg of crude material. 153.4 mg of the crude material was PEGylated ARC5690 aptamer, which is a purity of 70.2%. FIG. 2 is a Strong Anion eXchange HPLC trace of a sample of the crude material from the PEGylation reaction, which shows the PEGylated ARC5690 aptamer and impurities.

Figure 3:
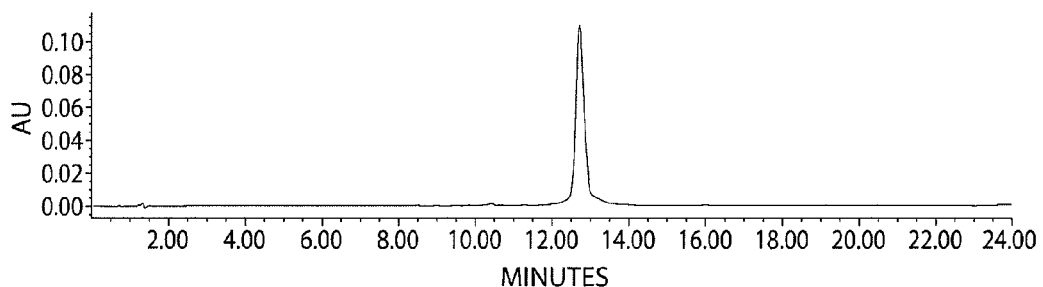
FIG. 3 is a SAX trace of the material that flowed through upon loading the ARC5690 PEGylation reaction mixture to the Q Sepharose® column.

The PEGylated ARC5690 aptamer was diluted 2.5× with 100% $H_2O$. This material was loaded at 10 mL/min onto a 20 mL column containing Q Sepharose® Fast Flow media (GE Healthcare) and the column was washed with 100% $H_2O$. The diluted PEGylated reaction mixture was flowed through the column and the column was then washed with one column volume of 100% $H_2O$. The eluted reaction mixture and column wash was collected and designated Fraction 1. A Strong Anion eXchange HPLC trace of a sample of Fraction 1 is shown in FIG. 3. Of the 113 mg of material collected in Fraction 1, 110 mg was PEGylated ARC5690 aptamer, which is a purity of 97%.

Figure 4:
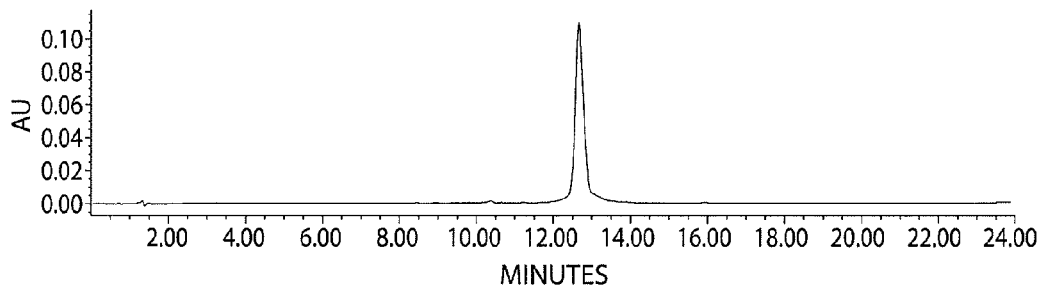
FIG. 4 is a SAX trace of the material of Fraction 2 described in Example 2.
Figure 5:
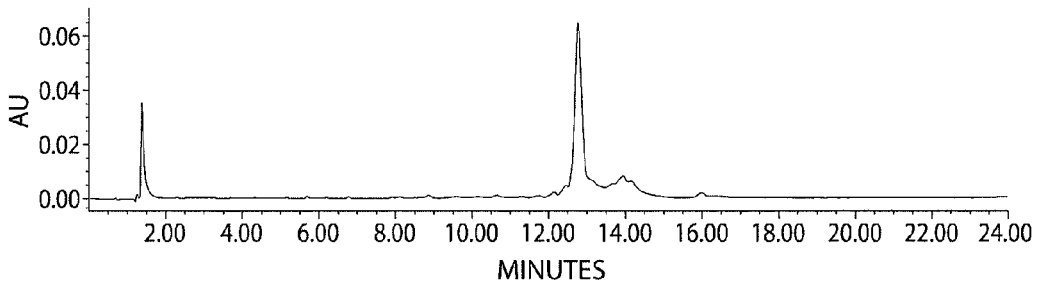
FIG. 5 is a SAX trace of the material of Fraction 3 described in Example 2.

In order to determine what material was left behind on the column after collecting Fraction 1, the column was washed with 60% of 100% $H_2O$ and 40% of a buffer containing 1.5 mM NaCl and 20 mM sodium phosphate, pH 7.0. Two peaks eluted and were collected and designated Fraction 2 and Fraction 3, respectively. Strong Anion eXchange HPLC traces of samples of Fractions 2 and 3 are shown in FIGS. 4 and 5, respectively. Of the 24 mg of material collected in Fraction 2, 23.3 mg was PEGylated ARC5690 aptamer, which is a purity of 97%. In contrast, of the 18 mg of material collected in Fraction 3, only 10.3 mg was PEGylated ARC5690 aptamer, which is a purity of 57%.

These data show that the flow through and 100% $H_2O$ column wash, designated as Fraction 1, produced a high yield of very pure (97%) PEGylated ARC5690. Furthermore, analysis of the resin bound material allows for insight into the impurity profile, the sequence, as well as the specificity of the PEGylation reaction.

Example 3

Purification of an Aptamer

Figure 8:
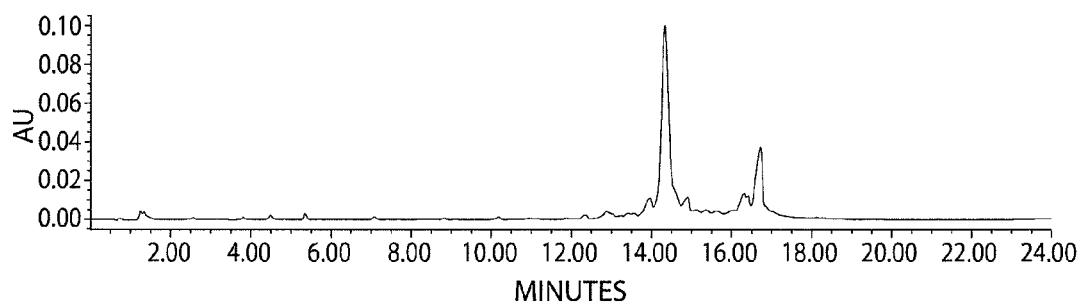
FIG. 8 is a SAX trace of the crude ARC5692 PEGylation reaction mixture prior to the purification described in Example 3.

The ARC5692 aptamer (a 39 mer) was synthesized and PEGylated as described in Example 1 with a 40 kDa PEG yielding 1,791 mg of crude material. 913 mg of the crude material was PEGylated ARC5692 aptamer, which is a purity of 51%. FIG. 8 is a Strong Anion eXchange HPLC trace of a sample of the crude material from the PEGylation reaction, which shows the PEGylated ARC5692 aptamer and impurities.

Figure 6:
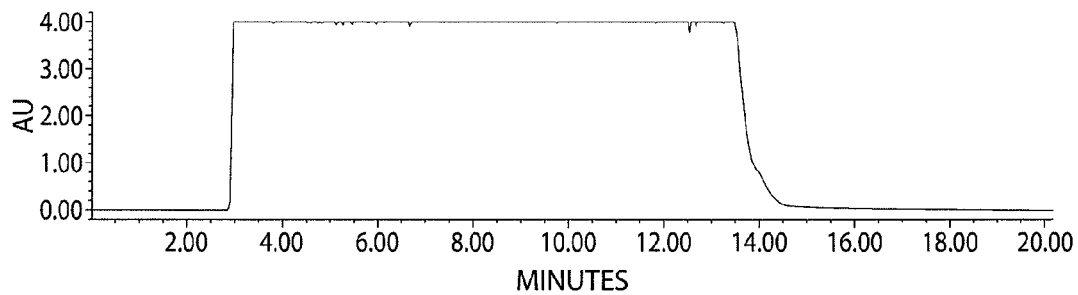
FIG. 6 is a chromatogram from a preparative Q Sepharose® column following loading of the ARC5692 PEGylation reaction mixture.
Figure 9:
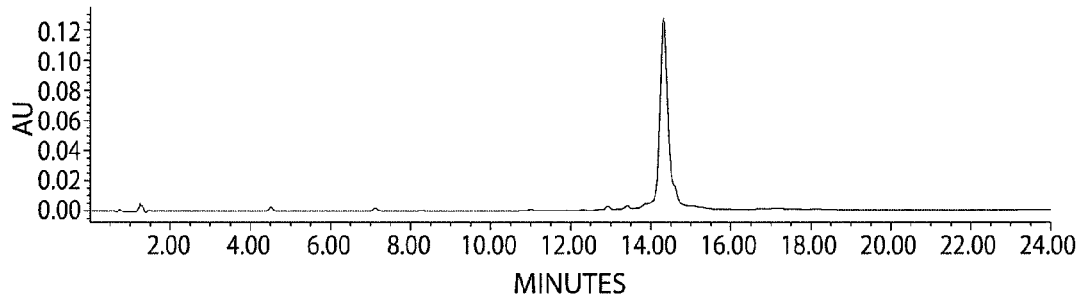
FIG. 9 is a SAX trace of the material that flowed through upon loading the ARC5692 PEGylation reaction mixture to the Q Sepharose® column.

The PEGylated ARC5692 aptamer was diluted 2.5× with 100% $H_2O$. This material was loaded at 50 mL/min onto a 255 mL column containing Q Sepharose® Fast Flow media (GE Healthcare) and the column was washed with 100% $H_2O$. A chromatogram of the optical density at 270 nm ($OD_{270}$) of the diluted PEGylated reaction mixture is shown in FIG. 6. The diluted PEGylated reaction mixture and one column volume of 100% $H_2O$ wash was flowed through the column and was collected. A Strong Anion eXchange HPLC trace of an aliquot of this eluent is shown in FIG. 9. Of the 901 mg of material collected in this flow through, 829 mg was PEGylated ARC5692 aptamer, which is a purity of 92%.

Figure 7:
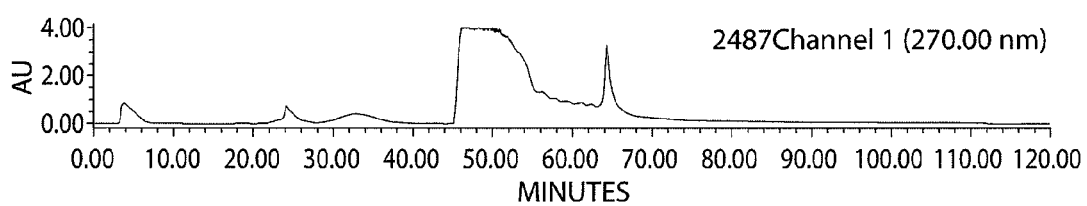
FIG. 7 is a chromatogram from a preparative Q Sepharose® column during the isocratic gradient run as described in Example 3.

In order to determine what material was left behind on the column after collecting the aforementioned first elution, an isocratic gradient was run according to Table 1, where Buffer A was 100% $H_2O$ and Buffer B was 1.5 mM NaCl and 20 mM Sodium Phosphate, pH 7.0. A chromatogram at an $OD_{270}$ of the material that eluted from the column is shown in FIG. 7. The peaks that were collected are listed in Table 2. Peaks 4 and 5 were pooled as one fraction and designated Peaks 4/5. Of the 12.4 mg of material collected in Peak 1, 10.7 mg was PEGylated ARC5692 aptamer, which is a purity of 86%.

TABLE 1

Q Sepharose ® Isocratic Gradient Run

| Time (minutes) | Flow Rate (mL/min) | Buffer A (%) | Buffer B (%) |
|---|---|---|---|
| 1-12 | 50 | 90 | 10 |
| 12-19 | 75 | 80 | 20 |
| 19-41 | 75 | 75 | 25 |
| 41-68 | 75 | 50 | 50 |
| 68-90 | 75 | 0 | 100 |

TABLE 2

Q Sepharose ® Fractions Collected

| Peak | Time (minutes) | Buffer A (%) | Buffer B (%) |
|---|---|---|---|
| 1 | 3-7 | 90 | 10 |
| 2 | 22-24 | 75 | 25 |
| 3 | 29-38 | 75 | 25 |
| 4 | 46-64 | 50* | 50 |
| 5 | 64-66 | 50* | 50 |

*Peaks 4 and 5 were pooled as one fraction

Figure 10:
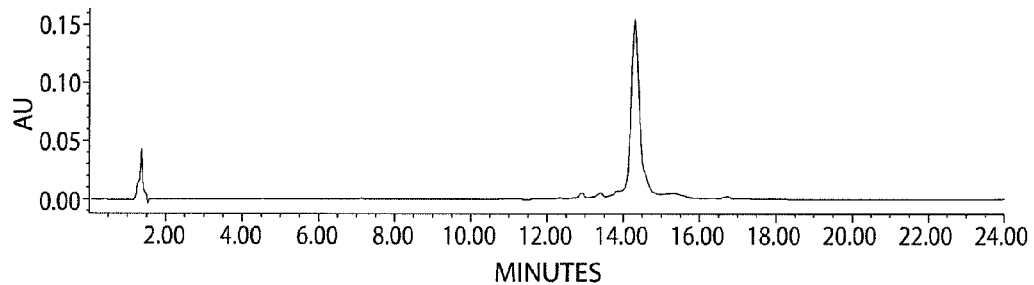
FIG. 10 is a SAX trace of the material of Peak 1 described in Example 3.
Figure 11:
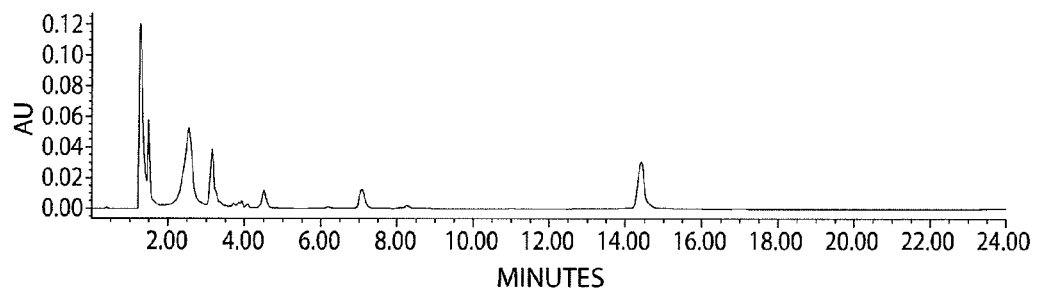
FIG. 11 is a SAX trace of the material of Peak 2 described in Example 3.
Figure 12:
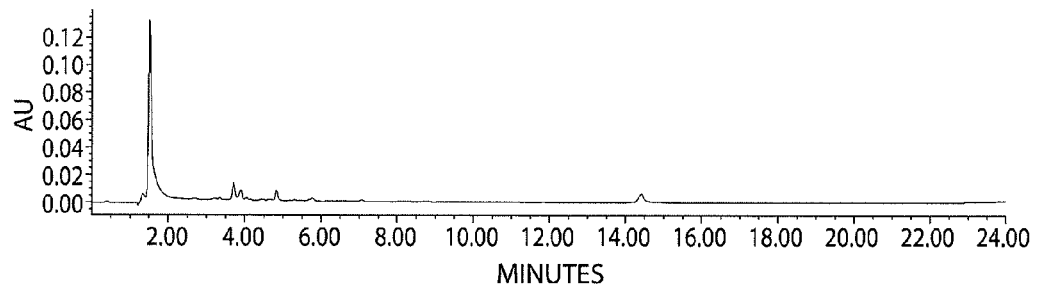
FIG. 12 is a SAX trace of the material of Peak 3 described in Example 3.
Figure 13:
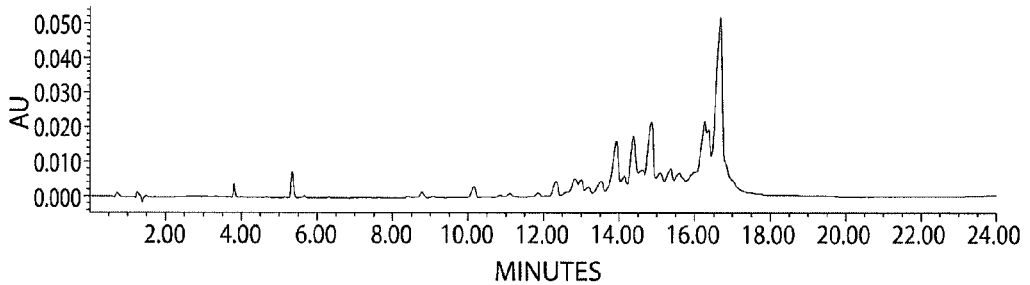
FIG. 13 is a SAX trace of the material of Peak 4/5 described in Example 3.

A Strong Anion exchange HPLC trace of a sample of Peak 1 is shown in FIG. 10. In contrast, most of the material collected in Peak 2, Peak 3 and Peaks 4/5, only 10.3 mg was not PEGylated ARC5692 aptamer. Strong Anion exchange HPLC traces of samples of Peak 2, Peak 3 and Peaks 4/5 are shown in FIGS. 11, 12 and 13, respectively.

Once again, these data show that the flow through and the 100% $H_2O$ column wash produced a high yield of very pure (92%) PEGylated ARC5692. Furthermore, about 1% of the material bound to the column was collected in Peak 1.

Example 4

Purification of an Aptamer

Figure 14:
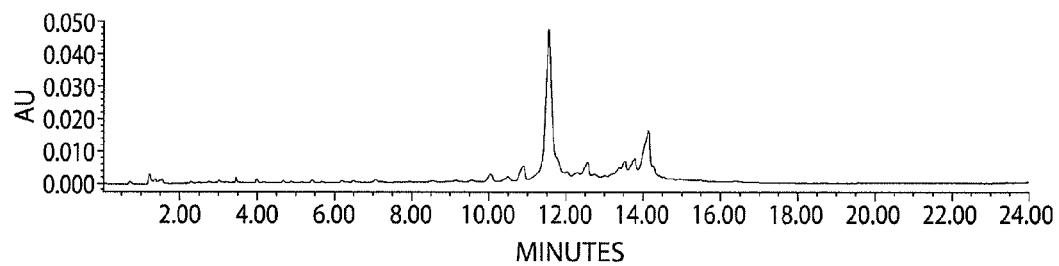
FIG. 14 is a SAX trace of the crude ARC594 PEGylation reaction mixture prior to the purification described in Example 4.

The ARC594 aptamer (a 36 mer) was synthesized and PEGylated as described in Example 1 with a 40 kDa PEG yielding 4,706 mg of crude material. 2,094 mg of the crude material was PEGylated ARC594 aptamer, which is a purity of 44.5%. FIG. 14 is a Strong Anion eXchange HPLC trace of a sample of the crude material from the PEGylation reaction, which shows the PEGylated ARC594 aptamer and impurities.

Figure 15:
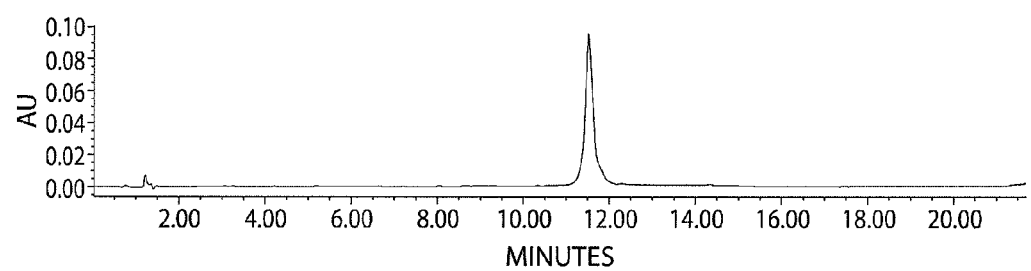
FIG. 15 is a SAX trace of the material that flowed through upon loading the ARC594 PEGylation reaction mixture to the Q Sepharose® column.

The PEGylated ARC594 aptamer was diluted 2.5× with 100% $H_2O$. This material was loaded at 100 mL/min onto a 255 mL column containing Q Sepharose® Fast Flow media (GE Healthcare) and the column was washed with 100% $H_2O$. The diluted PEGylated reaction mixture was flowed through the column and the column was then washed with one column volume of 100% $H_2O$. The eluted reaction mixture and column wash was collected and designated Fraction 1. A Strong Anion eXchange HPLC trace of a sample of Fraction 1 is shown in FIG. 15. Of the 1,431 mg of material collected in Fraction 1, 1,374 mg was PEGylated ARC594 aptamer, which is a purity of 96%.

Figure 16:
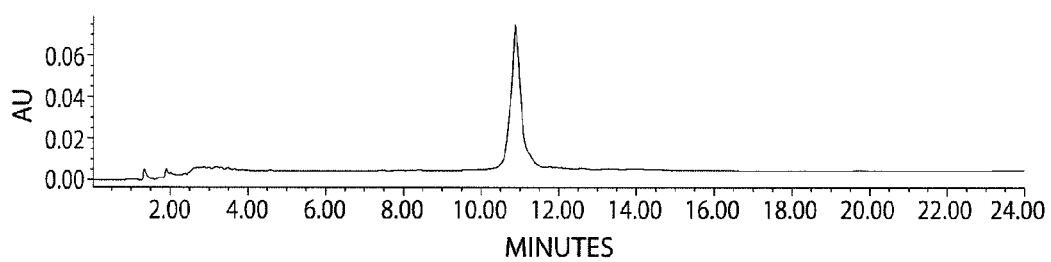
FIG. 16 is a SAX trace of the material of Fraction 2 described in Example 4.
Figure 17:
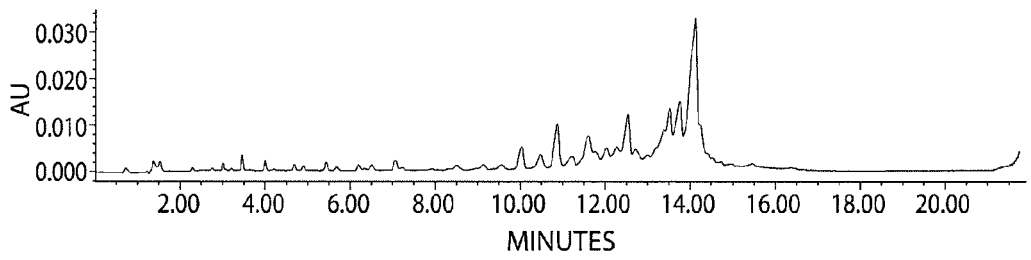
FIG. 17 is a SAX trace of the material of Fraction 3 described in Example 4.
Figure 18:
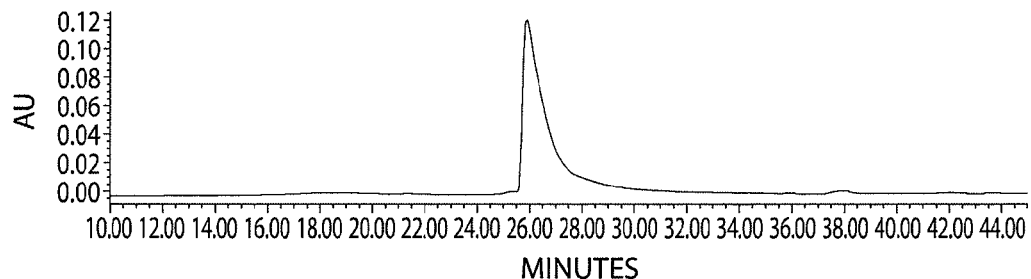
FIG. 18 is a reverse phase HPLC UV trace of unPEGylated human serum albumin (HSA) 16 mg/mL (5 µL injection).
Figure 19:
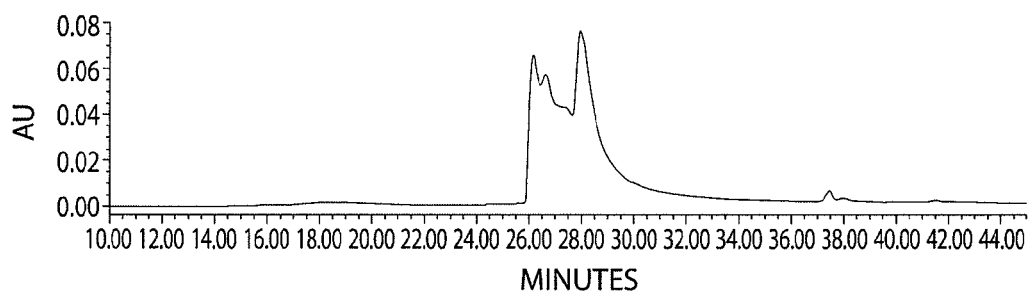
FIG. 19 is a reverse phase HPLC UV trace of an HSA PEG reaction/purification starting material 4 mg/mL (50 µL injection).
Figure 20:
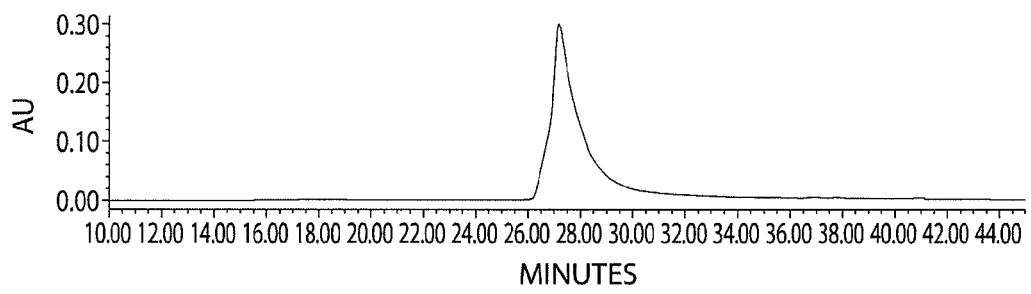
FIG. 20 is a reverse phase HPLC UV trace of a 40K-PEGylated HSA containing fraction that flowed over the Q Sepharose® column 15 mg/mL (50 µL injection).
Figure 21:
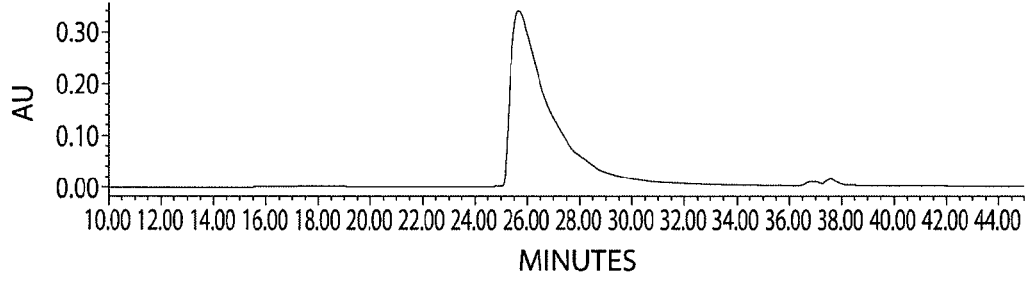
FIG. 21 is a reverse phase HPLC UV trace of an unPEGylated HSA containing fraction that bound the Q Sepharose® column 15 mg/mL (50 µL injection).
Figure 22:
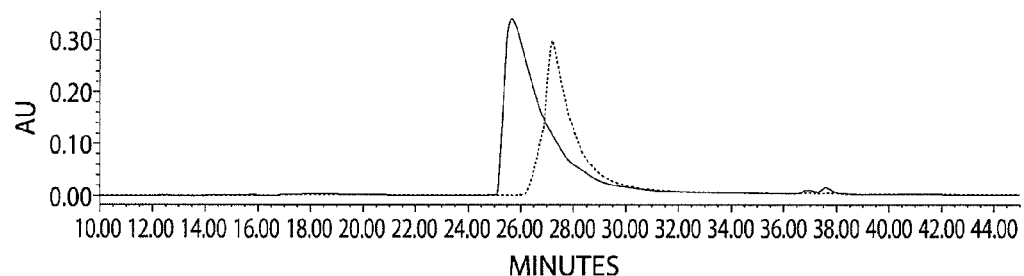
FIG. 22 is an overlay of FIG. 20 (PEGylated HSA containing fraction) and FIG. 21 (unPEGylated HSA containing fraction).
Figure 23:
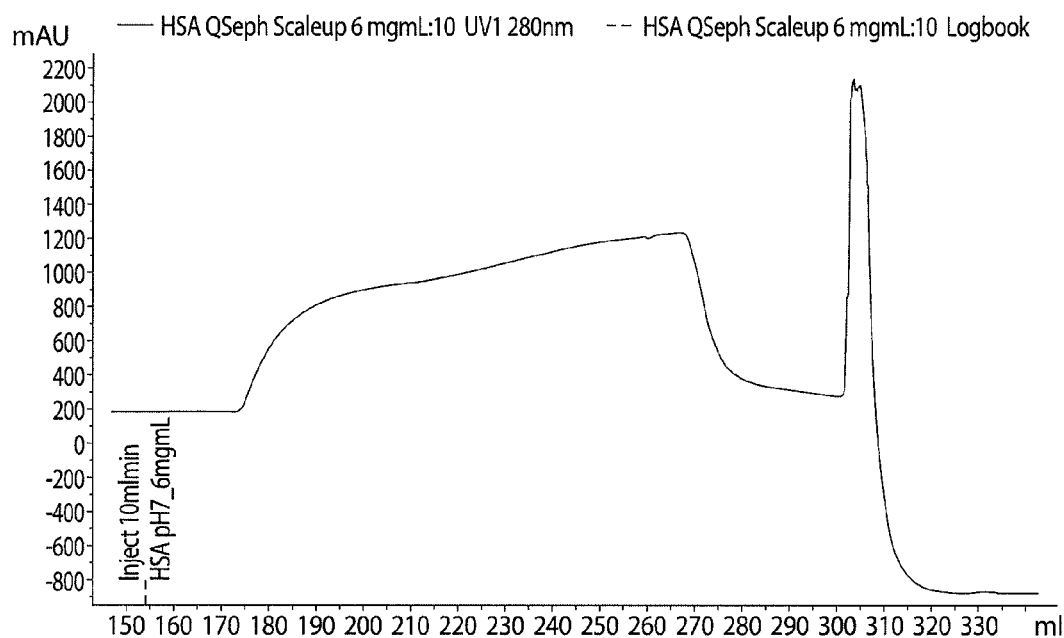
FIG. 23 is a preparatory HPLC trace from Load and Flow purification of human serum albumin 6 mg/ml.
Figure 24:
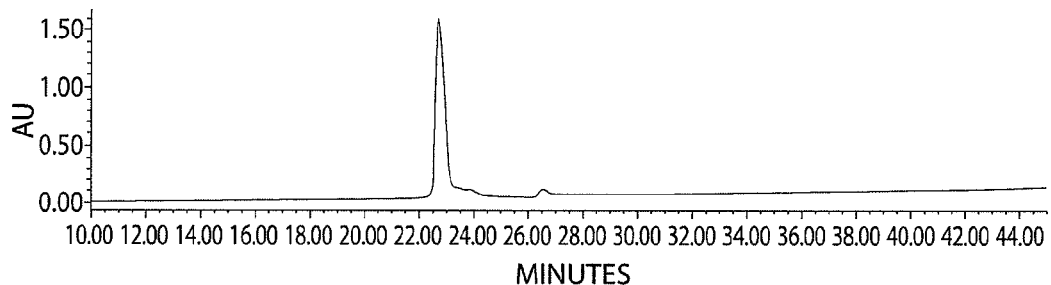
FIG. 24 is a reverse phase HPLC UV trace of unPEGylated Insulin 6 mg/mL (2.5 µL injection).
Figure 25:
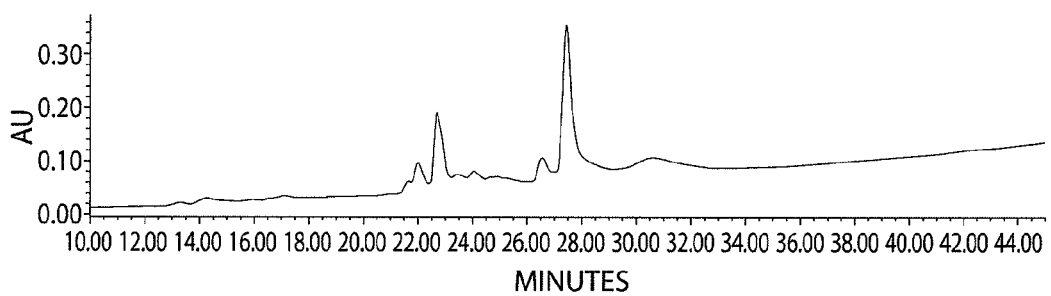
FIG. 25 is a reverse phase HPLC UV trace of an Insulin PEG reaction/purification starting material 1 mg/mL (50 µL injection).
Figure 26:
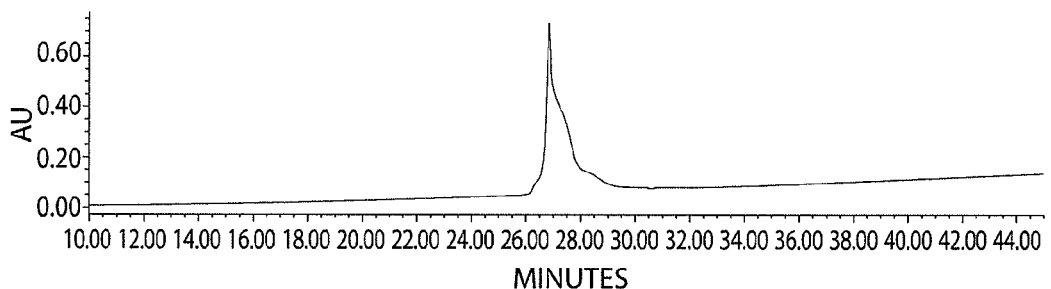
FIG. 26 is a reverse phase HPLC UV trace of a fraction containing 40K-PEGylated Insulin that flowed over the SP Sepharose® column 5 mg/mL (50 µL injection).
Figure 27:
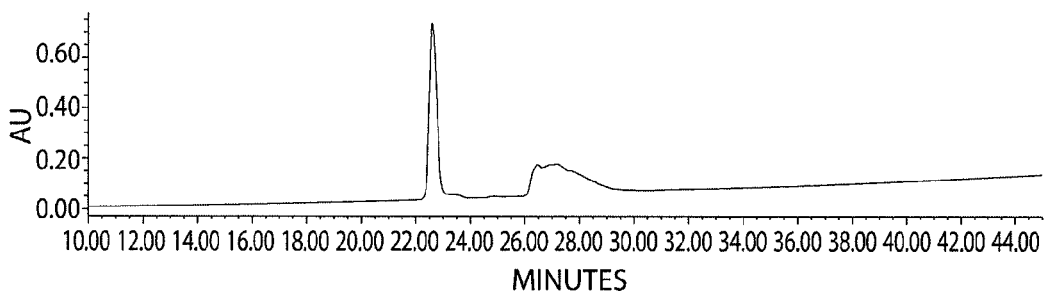
FIG. 27 is a reverse phase HPLC UV trace of a fraction containing unPEGylated Insulin that bound the SP Sepharose® column 5 mg/mL (50 µL injection).
Figure 28:
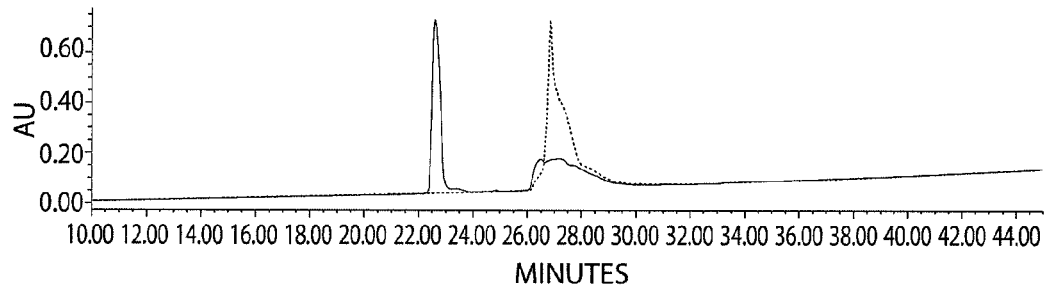
FIG. 28 is an overlay of FIG. 26 (PEGylated Insulin containing fraction) and FIG. 27 (unPEGylated Insulin containing fraction).
Figure 29:
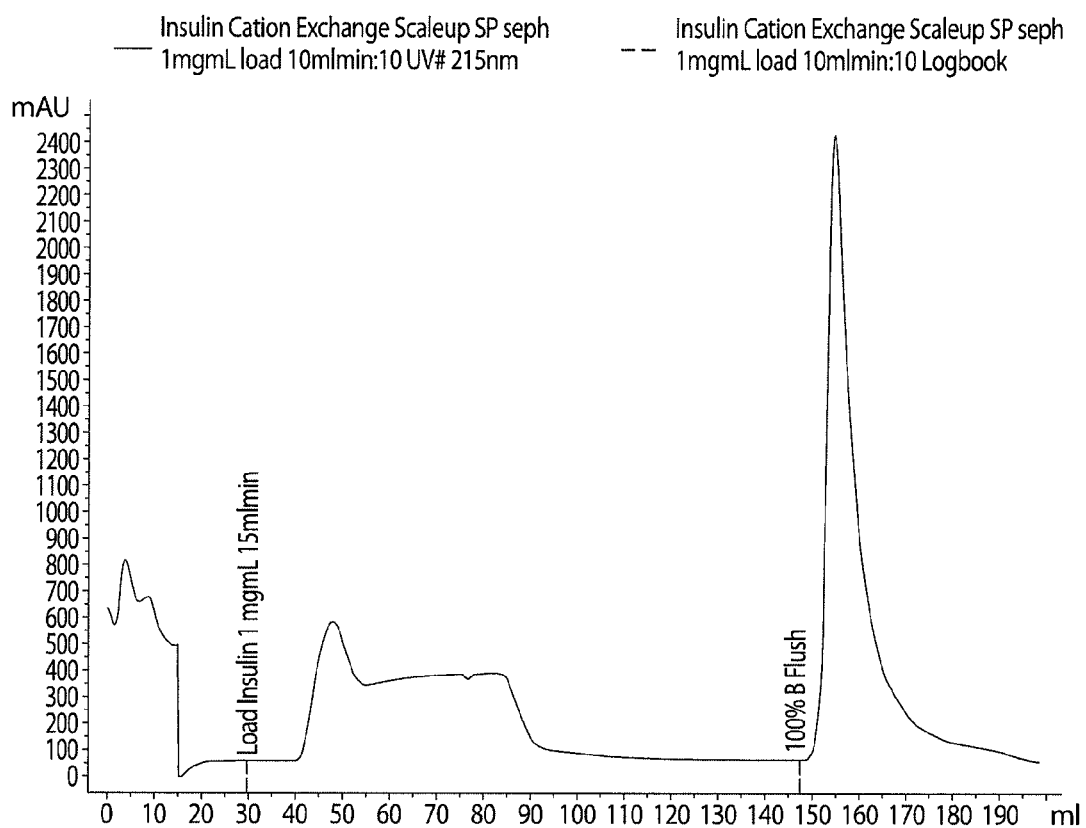
FIG. 29 is a preparatory HPLC trace from Load and Flow purification of Insulin 1 mg/ml.

In order to determine what material was left behind on the column after collecting the aforementioned first fraction, the column was washed with 90% of 100% $H_2O$ and 10% of a buffer containing 1.5 mM NaCl and 20 mM sodium phosphate, pH 7.0. The material that eluted was collected and designated Fraction 2. A Strong Anion eXchange HPLC trace of a sample of Fraction 2 is shown in FIG. 16. The column was then washed with 60% of 100% $H_2O$ and 40% of a buffer containing 1.5 mM NaCl and 20 mM sodium phosphate, pH 7.0. The material that eluted was collected and designated Fraction 3. A Strong Anion eXchange HPLC trace of a sample of Fraction 3 is shown in FIG. 17. Of the 71 mg of material collected in Fraction 2, 60 mg was PEGylated ARC594 aptamer, which is a purity of 84%. In contrast, of the 2,970 mg of material collected in Fraction 3, only trace amounts of PEGylated ARC594 were detected.

Once again, these data show that the 100% $H_2O$ first elution produced a high yield of very pure (92%) PEGylated ARC594, and only a fraction (4%) of the desired material actually bound to the column.

Example 5

Purification of an Aptamer

To begin, 320 g of crude ARC5692 (a 39 mer) PEGylation reaction at 49% purity (157 g of ARC5692 PEGylated full length product) was loaded onto a 20 cm diameter HPLC column packed with 17.7 L of Q Sepharose FF resin. The column was equilibrated at 70° C. with water for injection (WFI) at a flow rate of 600 mL/min. The flowover contained 149 g of 83% pure PEGylated FLP (124 g). The recovery of ARC5692 was determined to be 79%.

Example 6

Batch Purification of an Aptamer

The ARC594 aptamer (a 36 mer) was synthesized and PEGylated as described in Example 1 with a 40 kDa PEG yielding 178 mg of crude material in 14 mL of 100% $H_2O$. Of the crude material, 78.3 mg was PEGylated aptamer, which is a purity of 44.0%. 25 mL of Q Sepharose® resin (GE Healthcare), preserved in 20% ethanol, were transferred into a 50 mL conical vial. The resin was allowed to settle undisturbed for 1 hour. The excess ethanol was poured off and an additional 10 mL of resin was added to give a total of ~15 mL of resin. The solution of crude material was then added to the 50 mL conical vial containing the resin. This tube was then vortexed for approximately 1 minute. After vortexing, the aptamer resin mixture was centrifuged at 4,350 RPM for 30 minutes. The supernatant was then poured off and filtered with a 0.22 μm filter to ensure that all resin was removed from the sample. 35 mg of 94% pure ARC594 was recovered from the supernatant.

Example 7

PEGylation and Purification of a Protein

A protein, such as lysozyme, can be conjugated to PEG as described in United States Patent Application Publication No. US2005-0089952. The PEGylation of proteins is typically accomplished with a succinimidyl propionate activated PEG (mPEG-SPA). A 150 μM solution of lysozyme (Sigma) is PEGylated with either 5, 20 or 30 kDa mPEG-SPA using a 2:1 PEG:lysozyme molar ratio for 65 minutes at room temperature in 25 mM sodium phosphate, pH 8. The PEGylated lysozyme is diluted 2.5× with 100% $H_2O$. This material is then loaded at 10 mL/min onto a 20 mL column containing Q Sepharose® Fast Flow media (GE Healthcare) and the column is washed with 100% $H_2O$. The diluted PEGylated reaction mixture is flowed through the column and the column is then washed with one column volume of 100% $H_2O$. The eluted reaction mixture and column wash is collected and designated Fraction 1. The column is then washed with 90% of 100% H$_2$O and 10% of a buffer containing 1.5 mM NaBr and 25 mM sodium phosphate, pH 8.0. The material that elutes is collected and designated Fraction 2.

Example 8

PEGylation and Purification of a Protein

PEGylation:

To begin, 5 g of lyophilized human serum albumin (HSA) was dissolved in water at a concentration of 20 mg/mL. To prepare albumin that contains no mixed disulfides (mercaptalbumin) and has a free thiol group at Cys-34, 5 equivalents (58 mg) of dithiothreitol (DTT) was added to the HSA solution and was allowed to react for 12 hours at ambient temperature. The solution was then diafiltered with water using a Polyethersulfone 5 kDa MW cutoff membrane to remove the DTT. After ultrafiltration, the concentration was 25 mg/mL and the volume was 200 mL. 25 mL of sodium phosphate buffer, pH 8, was then added to the reaction. Two equivalents of Y-shaped maleimide activated m-PEG 40 kDa (6 g) were dissolved in 30 mL of acetonitrile and the PEG solution was added to the buffered HSA solution. The reaction was allowed to proceed at ambient temperature overnight to ~50% completion and the reaction progress was monitored by analytical reverse phase HPLC.

Load and Flow Purification:

Approximately 600 mg of PEGylation reaction (1:1 PEGylated HSA: unPEGylated HSA) was loaded onto a 5 mL GE Healthcare HiTrap Q Sepharose FF column equilibrated with 20 mM sodium phosphate, pH 7.2, (eluent A) at 25° C. at 10 mL/min. Approximately 280 mg of PEGylated HSA flowed over the column. The column was washed with 20 mM sodium phosphate, pH 7.2. Following the column wash, ~300 mg of unPEGylated HSA was eluted off the column with 1.5 M sodium chloride, 20 mM sodium phosphate (eluent B), pH 7. All fractions were quantified by UV spectroscopy at 280 nm and analyzed by reverse phase HPLC.

Analytical HPLC Parameters for HSA:
Instrument used: Waters Alliance Bio HPLC System
Column Used Phenomenex Gemini 3 μm C-18 110 Å (150× 2.0 mm)
Mobile Phase A: 0.1% trifluoroacetic acid in water
Mobile Phase B: 0.1% trifluoroacetic acid in acetonitrile
UV wavelength: 280 nm
Gradient:

|   | Time (min) | Flow (mL/min) | % A | % B | Curve |
|---|---|---|---|---|---|
| 1 | 0.01 | 0.20 | 100.0 | 0.0 | 6 |
| 2 | 2.10 | 0.20 | 100.0 | 0.0 | 6 |
| 3 | 27.10 | 0.20 | 50.0 | 50.0 | 6 |
| 4 | 52.10 | 0.20 | 0.0 | 100.0 | 6 |
| 5 | 55.00 | 0.20 | 0.0 | 100.0 | 6 |
| 6 | 55.20 | 0.20 | 100.0 | 0.0 | 6 |
| 7 | 59.00 | 0.20 | 100.0 | 0.0 | 6 |

The data for this example are presented in FIGS. 18-23.

Example 9

PEGylation and Purification of a Protein

PEGylation:

To begin, 600 mg of lyophilized bovine insulin was dissolved in 0.02 M sodium acetate 0.2 M sodium chloride, pH 4, to a concentration of 1 mg/mL. Two equivalents of Y-shaped aldehyde activated m-PEG 40 kDa (8.4 g) were added to the buffered insulin solution. Thirty equivalents (with respect to insulin) of sodium cyanoborohydride were added to the insulin solution and the reaction was allowed to proceed for 12 hours at ambient temperature. To quench this reaction, 63 grams of lysine was added to the reaction. The reaction was then diafiltered with 0.02 M sodium acetate using a Polyethersulfone 5 kDa MW cutoff membrane.

Load and Flow Purification:

Approximately 50 mg (1 mg/mL) of the ultrafiltered PEGylation reaction was loaded onto a 5 mL GE Healthcare HiTrap SP Sepharose FF cation exchange column equilibrated with 20 mM sodium acetate, pH 4, at 25° C. at 15 mL/min. Approximately 20 mg of 40K PEGylated insulin flowed over the column. The column was washed with 20 mM sodium acetate, pH 4. Following the column wash, 35 mg of unPEGylated insulin bound to the column and was eluted off with 0.5 M sodium chloride, 20 mM sodium acetate, pH 4. All fractions were quantified by UV spectroscopy at 220 nm and analyzed by reverse phase HPLC.

Analytical HPLC Parameters for Insulin:
Instrument used: Waters Alliance Bio HPLC System
Column Used Phenomenex Gemini 3 μm C-18 110 Å (150× 2.0 mm)
Mobile Phase A: 0.1% trifluoroacetic acid in water
Mobile Phase B: 0.1% trifluoroacetic acid in acetonitrile
UV wavelength: 220 nm
Gradient:

|   | Time (min) | Flow(mL/min) | % A | % B | Curve |
|---|---|---|---|---|---|
| 1 | 0.01 | 0.20 | 100.0 | 0.0 | 6 |
| 2 | 2.10 | 0.20 | 100.0 | 0.0 | 6 |
| 3 | 27.10 | 0.20 | 50.0 | 50.0 | 6 |
| 4 | 52.10 | 0.20 | 0.0 | 100.0 | 6 |
| 5 | 55.00 | 0.20 | 0.0 | 100.0 | 6 |
| 6 | 55.20 | 0.20 | 100.0 | 0.0 | 6 |
| 7 | 59.00 | 0.20 | 100.0 | 0.0 | 6 |

The data for this example are presented in FIGS. 24-29.

Example 10

Batch Mode Protocols for Purifying an Aptamer

The following two batch mode protocols were used to purify ARC7299 (a 37 mer).

Figure 30:
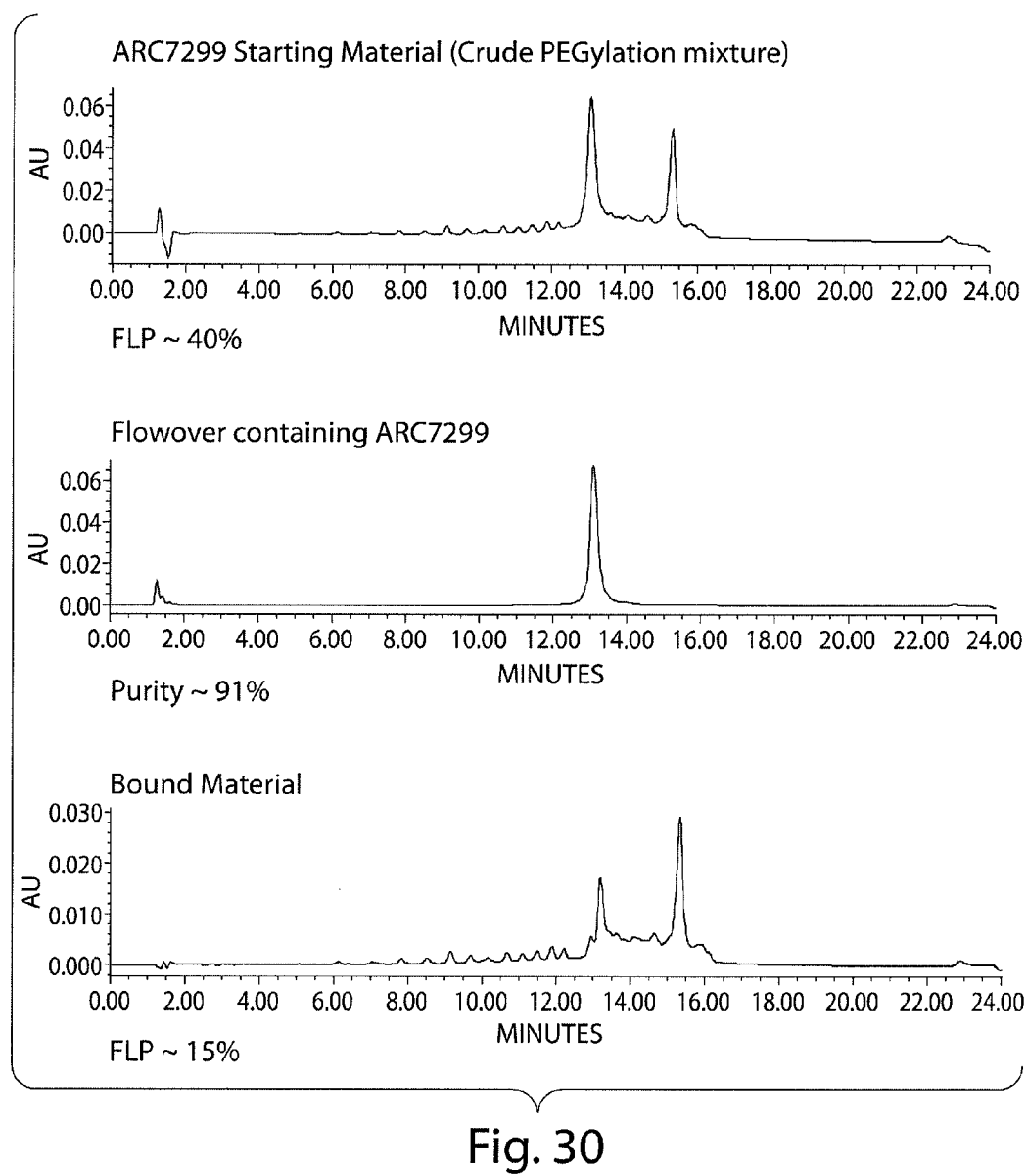
FIG. 30 (top) shows the crude PEGylation mixture of the ARC7299 starting material, wherein the full length product is present at about 40%.

Using heat for oligonucleotide denaturation, the protocol was as follows:

1) A quenched PEGylation reaction mixture at an oligonucleotide concentration of 5 mg/mL containing 375 mg of crude material, 40% (150 mg) of which was PEGylated full length product was purified using batch mode Load and Flow (see FIG. 30 (top)). To begin, an appropriate amount of resin was determined in terms of the unPEGylated material abundance. Here 60% (225 mg) of the oligonucleotide content in the reaction mixture was unPEGylated and a resin volume of 10 mL was used (22.5 mg of unPEGylated material/ml of resin loading). The correct amount of resin was prepared using the following steps:

a) 50 mL of slurried bulk resin (in 20% ethanol from manufacturer) was added to a conical vial and centrifuged for 30 minutes or let it gravity settle, b) supernatant from settled resin was poured off and excess resin was removed until 10 mL remained in order to achieve the correct loading, c) the resin was reslurried in 10 mL of water and centrifuged for 30 minutes, d) supernatant was poured off from the settled resin and then 10 mL of 1.5 M sodium chloride was added to the resin, and the mixture was reslurried, e) supernatant was poured off from the settled resin and then 10 mL of water was added to the resin and the mixture was reslurried, f) step "e" was repeated twice to ensure all salt is removed from resin, g) 2 mL of water was added to the settled resin and the mixture was shaken to re-suspend the resin and achieve a slurry and transferred into a Schott bottle;

The aforementioned crude PEGylated reaction mixture was transferred to the Schott bottle containing the prepared resin. The contents were thoroughly mixed at 80° C. for 20 minutes. The mixture was then filtered and the resin was washed with 80° C. water. The filtrate was collected and analyzed by UV spectroscopy and analytical SAX HPLC. 80% (120 mg) of ARC7299 was recovered at a purity of 91% (FIG. 30 (middle)). To elute the unPEGylated impurities captured on the resin, the resin was washed with each of the following eluents: 80° C. 500 mM sodium chloride, 80° C. 1 M sodium chloride, and 80° C. 1.5 M sodium chloride, respectively collecting the filtrates of all of these elutions as one fraction (FIG. 30 (bottom)).

FIG. 30 (top) shows the crude PEGylation mixture of the ARC7299 starting material, wherein the full length product is present at about 40%. FIG. 30 (middle) shows the flowover containing ARC7299, which is approximately 91% pure. FIG. 30 (bottom) shows the material bound to the resin, which contains about 15% full length product. Overall, FIG. 30 shows that the method achieves a high level of purification.

Example 11

Solid Phase Extraction Protocol

The following two batch mode protocols were used to purify ARC5692 (a 39 mer).

Figure 31:
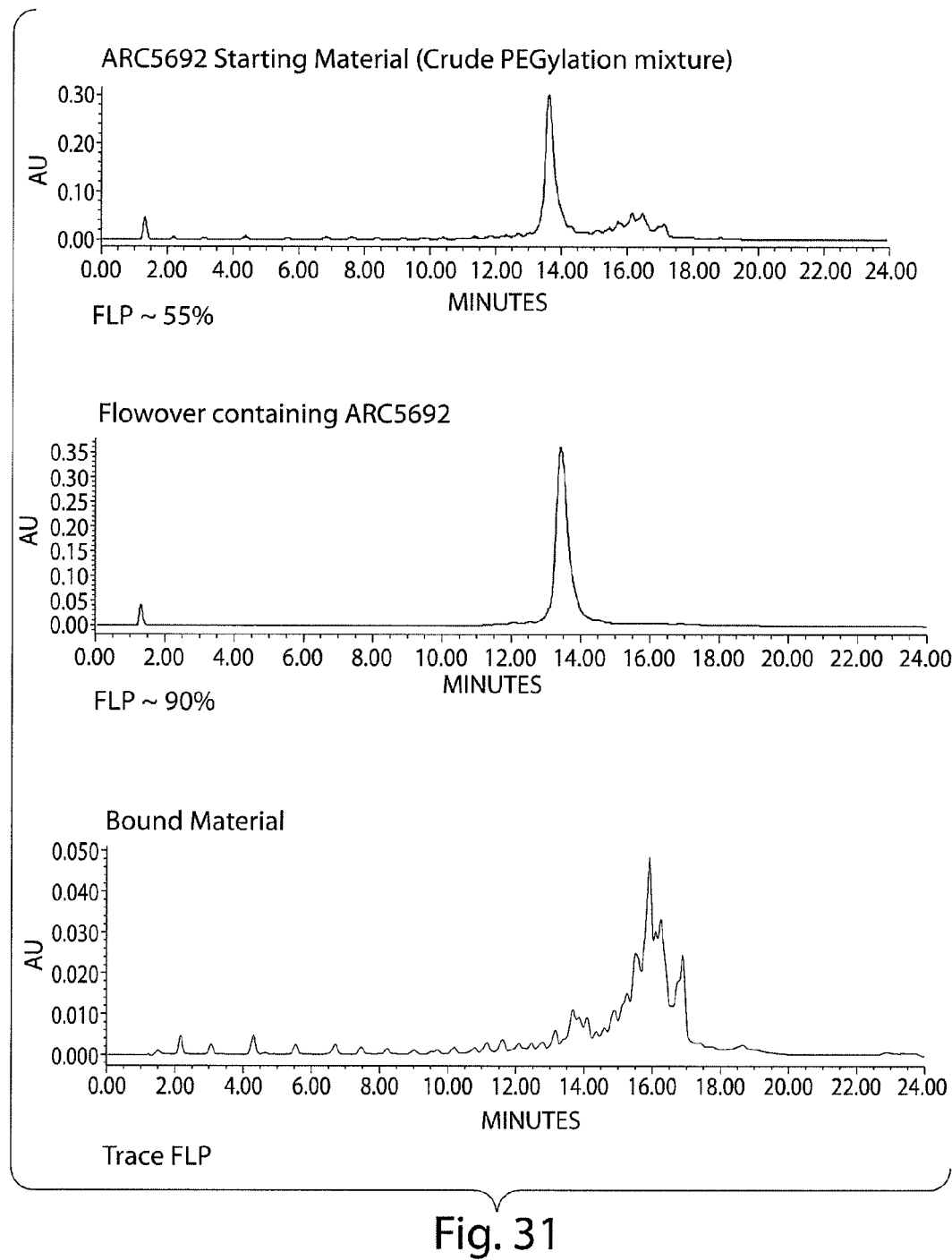
FIG. 31 (top) shows the crude PEGylation mixture of the ARC5692 starting material, wherein the full length product is present at about 55%.

Using heat for oligonucleotide denaturation, protocol was as follows:

A quenched PEGylated reaction mixture at an oligo concentration of 5 mg/mL containing 1 g of crude material, 55% (550 mg) of which was PEGylated full length product was purified using the solid phase extraction variation of Load and Flow (see FIG. 31 (top)). To begin, an appropriate amount of resin was determined in terms of the unPEGylated material abundance. Here 45% (450 mg) of the oligonucleotide content in the reaction mixture was unPEGylated and a resin volume of 15 mL was used (30 mg of unPEGylated material/mL of resin loading). A 25 mL Isolute® SPE reservoir was packed with 15 mL of settled resin. To equilibrate the column. Three column volumes of water were run over the column at ambient temperature. Twenty column volumes of 80° C. water were then flowed over the column. Three column volumes of 80° C. 1.5 M sodium chloride were then flowed over the column, followed by ten column volumes of 80° C. water over the column to re-equilibrate the column. The aforementioned PEGylation reaction was heated to 80° C. for 20 minutes and then loaded onto the column. The flowover was collected in one fraction. After loading, three column volumes of 80° C. water were flowed over the column to elute the rest of the desired PEGylated full length product (FLP) and the flowover was collected in the same fraction, and analyzed by UV spectroscopy and analytical SAX HPLC. This fraction (see FIG. 31 (middle)) contained 93% (512 mg) of the loaded ARC5692 at 90% purity. To elute the unPEGylated impurities captured on the resin, three column volumes of each of the following eluents were used sequentially: 80° C. 500 mM sodium chloride, 80° C. 1 M sodium chloride, and 80° C. 1.5 M sodium chloride. All of these elutions were collected as one fraction (see FIG. 31 (bottom)).

FIG. 31 (top) shows the crude PEGylation mixture of the ARC5692 starting material, wherein the full length product is present at about 55%. FIG. 31 (middle) shows the flowover containing ARC5692, which is approximately 90% pure. FIG. 31 (bottom) shows the material bound to the resin, which contains trace amounts of full length product. Overall, FIG. 31 shows that the method achieves a high level of purification.

Example 12

Load and Flow vs. Gradient-Based Ion Exchange Chromatography

Two 1.5 mmol syntheses of ARC594 were performed in parallel. One synthesis was worked up and purified using a traditional gradient-based ion exchange separation and the other utilized the Load and Flow methodology of the present invention. The batch that utilized Load and Flow yielded 4.2 g of 94% pure product while the batch using gradient-based ion exchange purification yielded 2.6 g at 89% purity.

Those of skill in the art will recognize that the invention, having now been described by way of written description and example, can be practiced in a variety of embodiments, and that the description and examples above are for purposes of illustration and not for limitation of the claims.

What is claimed is:

1. A method for separating polyethylene glycol biopolymer conjugated molecules from unconjugated molecules comprising the steps:

a) applying a mixture containing a polyethylene glycol biopolymer conjugated molecule and an unconjugated molecule to a resin having a pore size and a charge that substantially captures the unconjugated molecule with such pore size that also substantially excludes the polyethylene glycol biopolymer conjugated molecule from the resin, wherein the unconjugated molecule is substantially captured by the resin and the polyethylene glycol biopolymer conjugated molecule is substantially excluded from the resin; and b) collecting the entire filtrate as a single fraction, thereby separating a polyethylene glycol biopolymer conjugated molecule from an unconjugated molecule in the absence of gradient chromatography, and recovering the polyethylene glycol biopolymer conjugated molecule.

2. The method of claim 1, wherein the molecule is selected from the group consisting of a peptide, a polypeptide, a protein, an oligonucleotide and an aptamer.

3. The method of claim 1, wherein the mixture is a crude reaction mixture comprising an unconjugated molecule, a polyethylene glycol biopolymer conjugated molecule and an unreacted polyethylene glycol biopolymer.

4. The method of claim 1, wherein the resin comprises a column.

5. The method of claim 4, wherein the column is a high performance liquid chromatography (HPLC) column.

6. The method of claim 1, wherein the resin is not contained in a column.

7. The method of claim 1, wherein the resin is an anion exchange resin.

8. The method of claim 1, wherein the resin is a cation exchange resin.

9. The method of claim 1, wherein the applying step comprises flowing the mixture over the resin.

10. The method of claim 1, wherein the mixture and resin are stirred or agitated to create a slurry.

11. The method of claim 1, wherein the mixture is diluted before being applied to the resin.

12. The method of claim 11, wherein the diluent is water, sodium hydroxide, solvent or buffer.

13. The method of claim 1, wherein the method further comprises the step of adding a denaturant to the mixture prior to applying the mixture to the resin.

14. The method of claim 1, wherein the method further comprises the step of separating the polyethylene glycol biopolymer conjugated molecule from an unreacted polyethylene glycol biopolymer.

15. The method of claim 14, wherein the separating is by HPLC, precipitation or liquid-liquid extraction.

16. The method of claim 1, wherein the method further comprises the step of analyzing the filtrate.

17. The method of claim 1, wherein the method further comprises the step of removing the biopolymer from the biopolymer conjugated molecule.

18. The method of claim 1, wherein the method further comprises performing an ultrafiltration step and a desalting step.

19. The method of claim 1, wherein the method further comprises the step of lyophilizing the polyethylene glycol biopolymer conjugated molecule.

20. A method for separating biopolymer conjugated molecules from unconjugated molecules comprising the steps:
   a) adding a denaturant to a mixture containing a biopolymer conjugated molecule and an unconjugated molecule;
   b) applying the mixture to a resin having a pore size and a charge that substantially captures the unconjugated molecule with such pore size that also substantially excludes the biopolymer conjugated molecule from the resin, wherein the unconjugated molecule is substantially captured by the resin and the biopolymer conjugated molecule is substantially excluded from the resin; and
   c) collecting the entire filtrate as a single fraction, thereby separating a biopolymer conjugated molecule from an unconjugated molecule in the absence of gradient chromatography, and recovering the biopolymer conjugated molecule.

21. The method of claim 20, wherein the molecule is selected from the group consisting of a peptide, a polypeptide, a protein, an oligonucleotide and an aptamer.

22. The method of claim 20, wherein the mixture is a crude reaction mixture comprising an unconjugated molecule, a biopolymer conjugated molecule and an unreacted biopolymer.

23. The method of claim 20, wherein the resin comprises a column.

24. The method of claim 23, wherein the column is a high performance liquid chromatography (HPLC) column.

25. The method of claim 20, wherein the resin is not contained in a column.

26. The method of claim 20, wherein the resin is an anion exchange resin.

27. The method of claim 20, wherein the resin is a cation exchange resin.

28. The method of claim 20, wherein the applying step comprises flowing the mixture over the resin.

29. The method of claim 20, wherein the mixture and resin are stirred or agitated to create a slurry.

30. The method of claim 20, wherein the mixture is diluted before being applied to the resin.

31. The method of claim 30, wherein the diluent is water, sodium hydroxide, solvent or buffer.

32. The method of claim 20, wherein the method further comprises the step of separating the biopolymer conjugated molecule from an unreacted biopolymer.

33. The method of claim 32, wherein the separating is by HPLC, precipitation or liquid-liquid extraction.

34. The method of claim 20, wherein the method further comprises the step of analyzing the filtrate.

35. The method of claim 20, wherein the method further comprises the step of removing the biopolymer from the biopolymer conjugated molecule.

36. The method of claim 20, wherein the method further comprises performing an ultrafiltration step and a desalting step.

37. The method of claim 20, wherein the method further comprises the step of lyophilizing the biopolymer conjugated molecule.

38. A method for separating biopolymer conjugated molecules from unconjugated molecules comprising the steps:
   a) applying a mixture containing a biopolymer conjugated molecule and an unconjugated molecule to a resin having a pore size and a charge that substantially captures the unconjugated molecule with such pore size that also substantially excludes the biopolymer conjugated molecule from the resin, wherein the unconjugated molecule is substantially captured by the resin and the biopolymer conjugated molecule is substantially excluded from the resin;
   b) collecting the entire filtrate as a single fraction; and
   c) removing the biopolymer from the biopolymer conjugated molecule, thereby separating a biopolymer conjugated molecule from an unconjugated molecule in the absence of gradient chromatography, and recovering the biopolymer conjugated molecule.

39. The method of claim 38, wherein the molecule is selected from the group consisting of a peptide, a polypeptide, a protein, an oligonucleotide and an aptamer.

40. The method of claim 38, wherein the mixture is a crude reaction mixture comprising an unconjugated molecule, a biopolymer conjugated molecule and an unreacted biopolymer.

41. The method of claim 38, wherein the resin comprises a column.

42. The method of claim 41, wherein the column is a high performance liquid chromatography (HPLC) column.

43. The method of claim 38, wherein the resin is not contained in a column.

44. The method of claim 38, wherein the resin is an anion exchange resin.

45. The method of claim 38, wherein the resin is a cation exchange resin.

46. The method of claim 38, wherein the applying step comprises flowing the mixture over the resin.

47. The method of claim 38, wherein the mixture and resin are stirred or agitated to create a slurry.

48. The method of claim 38, wherein the mixture is diluted before being applied to the resin.

49. The method of claim 48, wherein the diluent is water, sodium hydroxide, solvent or buffer.

50. The method of claim 38, wherein the method further comprises the step of adding a denaturant to the mixture prior to applying the mixture to the resin.

51. The method of claim 38, wherein the method further comprises the step of separating the biopolymer conjugated molecule from an unreacted biopolymer.

52. The method of claim 51, wherein the separating is by HPLC, precipitation or liquid-liquid extraction.

53. The method of claim 38, wherein the method further comprises the step of analyzing the filtrate.

54. The method of claim 38, wherein the method further comprises performing an ultrafiltration step and a desalting step.

55. The method of claim 38, wherein the method further comprises the step of lyophilizing the biopolymer conjugated molecule.

* * * * *